United States Patent [19]

Hiroshi et al.

[11] Patent Number: 5,427,113
[45] Date of Patent: Jun. 27, 1995

[54] BIOLOGICAL INFORMATION MEASURING SYSTEM

[76] Inventors: Motoyama Hiroshi, c/o Tamamitsu Jinjya, 11-1, Inokashira, 4-chome, Mitaka-shi, Tokyo 181; Kobayashi Keisuke, c/o 7th Samejimasou, 3-8, Tsuchihashi, 3-chome, Miyamae-ku, kawasaksi-shi, Kanagawa 213; Akasaka Fumio, 28-7, Miyashimohoncho 3-chome, Sagamihara-shi, Kanagawa 229; Itagaki Yoshiko, 16-8-803, Nanpeidai, Miyamae-ku, Kawasaki-shi, Kanagawa 213, all of Japan

[21] Appl. No.: 566,470
[22] PCT Filed: Feb. 17, 1989
[86] PCT No.: PCT/JP89/00162
   § 371 Date: Jun. 19, 1992
   § 102(e) Date: Jun. 19, 1992
[87] PCT Pub. No.: WO89/07417
   PCT Pub. Date: Aug. 24, 1989

[30] Foreign Application Priority Data

Feb. 20, 1988 [JP] Japan .................................. 63-36494
Oct. 11, 1988 [JP] Japan .................................. 63-284361

[51] Int. Cl.⁶ .................................................. A61B 5/04
[52] U.S. Cl. ................................. 128/734; 364/413.02
[58] Field of Search .............. 128/735, 734, 741, 907; 364/413.01, 413.02, 413.13

[56] References Cited

U.S. PATENT DOCUMENTS 3,971,366 7/1976 Motoyama .
4,016,870 4/1977 Lock .................................. 128/735
4,557,271 12/1985 Stoller et al. .................... 128/734
4,794,934 1/1989 Motoyama et al. ............... 128/734
4,817,628 4/1989 Zealear et al. .................. 128/741
4,940,060 7/1990 Gu et al. ........................... 128/735
5,092,344 3/1992 Lee .

FOREIGN PATENT DOCUMENTS 2813068 10/1979 Germany .
2917704A1 3/1981 Germany .
55-31967 3/1980 Japan .
57-1252 1/1982 Japan .
60-149977 8/1985 Japan .
0231379A1 10/1986 Japan .
62-324 1/1987 Japan .
62-148643 7/1987 Japan .

OTHER PUBLICATIONS

A. van Boxtel "Skin Resistance during Square-wave Electric Pulses of 1 to 10 mA" Med. & Biol. Eng. & Comput. 1977, 15, 679–687.

*Primary Examiner*—Stephen C. Pellegrino
*Assistant Examiner*—Guy V. Tucker
*Attorney, Agent, or Firm*—McGlew & Tuttle

[57] ABSTRACT

The biological information measuring system of this invention applies rectangular voltage pulses across at least a pair of electrodes attached to the surface of a living body, obtains, through the analysis of a transient current flowing across electrodes, current waveform parameters representing an equation approximating the waveform of the transient current, and calculates equivalent circuit parameters representing an electrical equivalent circuit across the electrodes. Using at least one type of these parameters as biological information, abnormality of the living body is detected.

18 Claims, 23 Drawing Sheets

$\ell$ (cm)

|     | 5TH CERVICAL VERTEBRA |
| 1 — | 6TH CERVICAL VERTEBRA |
| 2 — | 7TH CERVICAL VERTEBRA |
| 3 — | 1ST THORACIC VERTEBRA |
| 4 — | 2ND THORACIC VERTEBRA |
| 5 — | 3RD THORACIC VERTEBRA |
| 6 — | 4TH THORACIC VERTEBRA |
| 5 — | 5TH THORACIC VERTEBRA |
| 4 — | 6TH THORACIC VERTEBRA |
| 3 — | 7TH THORACIC VERTEBRA |
| 2 — | 8TH THORACIC VERTEBRA |
| 1 — |     |

FIG. 17 ns system for diagnosing the "Keiraku" and the function of an internal organ to which the Keiraku belongs on the basis of parameter values characterizing changes over time in the current obtained by applying a rectangular-wave pulse voltage of 1/1,000 seconds and less than 3 volts to a location,
BIOLOGICAL INFORMATION MEASURING SYSTEM

FIELD OF THE INVENTION

This invention relates to a biological information measuring system for obtaining information about a living body by measuring and analyzing dynamic electrical characteristics on and in the vicinity of the surface of the living body.

BACKGROUND OF THE INVENTION

Electrical measurement of the surface of a living body, the skin, for example, is important in the field of electrophysiology, and is being practically applied to a polygraph and various types of diagnostic instruments in acupuncture and moxibustion. It is known that when measuring the electrical characteristics of the skin, the magnitude of voltage being applied and the duration of voltage application have a significant influence on measurement results. Application of too high a voltage could cause the electrolysis of water and/or dielectric breakdown in and out of adjacent cells. Such irreversible phenomena become pronounced when voltage application lasts longer. Application of a voltage of 10 volts for a few seconds can hardly obtain satisfactory reproducibility in the measurement of the d-c resistance of the skin. That is, a d-c measurement by applying a voltage of approximately 10 volts is nothing more than a kind of breakdown test. In order to perform proper measurements in a range where Ohm's law holds, it is necessary to apply a lower voltage for a duration as short as possible.

The surface and the inside, i.e., internal organs, of a human body are strongly linked to each other with the autonomic nervous system. Any disturbance of an internal organ is therefore indicated by a paresthesia at a particular location of the body surface governed by the autonomic nerve belonging to the same vertebral segment. This is a phenomenon known as the viscerosensory reflex, which is frequently used as a diagnostic means. Furthermore, the human body is a total system in which not only individual organs and tissues are combined while maintaining independence with each other, but also autonomic nervous, hormone and other systems have extremely complicated and delicate effects upon each other via unknown interactions. The surface and inside of the body are linked to each other by means of an entire system of such interactions.

Medical electronic engineering has made remarkable progress in recent years to such an extent that modern medical science relies almost entirely on instrumental diagnosis. Most of these diagnostic instruments, however, are dedicated to local diagnosis of the inside of the human body using X rays, ultrasonic waves, etc. Prices of instruments as well as their operating costs are usually extremely high. Furthermore, these instruments often cause abnormal stimuli to the human body, and some of them may leave a certain degree of impairment after diagnosis in extreme cases.

In view of this, the present inventor et al developed and proposed an internal organ-autonomic nervous function diagnostic system for diagnosing the "Keiraku" and the function of an internal organ to which the Keiraku belongs on the basis of parameter values characterizing changes over time in the current obtained by applying a rectangular-wave pulse voltage of 1/1,000 seconds and less than 3 volts to a location, called the "Seiketsu" according to acupuncture/moxibustion medicine, on fingers and toes (Japanese Patent Publication 52-4878; U.S. Pat. No. 3,971,366). In the following, the system according to this proposal will be referred to as the prior-art system.

The phenomenon on which the prior-art system relies was novel and not publicly known. That is, an electric current I (t) corresponding to a rectangular-wave voltage applied to the skin is a transient current which reaches the maximum value immediately after voltage application, and then attenuates within only several tens of microseconds into an almost constant d-c component. FIG. 1 shows the waveform of this transient current. The maximum current flowing in the initial stage is called the pre-polarization current BP, and the eventually stabilized d-c current is called the post-polarization current AP; the BP being several dozen to a hundred times as large as the AP. It is concluded on the basis of various tests conducted later that this current flows inside the corium.

In addition to the AP and the BP, a total amount of charge participating in polarization IQ and a current attenuation time TC are defined as shown in FIG. 1. That is, the total charge IQ is defined as a shaded area in the figure, and the attenuation time TC as the time expressed by a point 120 at which a tangent 100 at the BP of the current curve intersects with a straight line 110 drawn at the AP value in parallel with the time axis. These four parameters BP, AP, TC, IQ are effective in the Keiraku diagnosis in acupuncture/moxibustion medicine. In the prior-art system, the diagnoses of the Keiraku and the functions of internal organs are carried out on the basis of these parameter values at each Seiketsu and the horizontal and vertical balances among them. In the following description of this Specification, these parameters will be referred to as the transient characteristic parameters.

The prior-art system is based on the principle of the Oriental medicine, in which changes in the functions of internal organs are grasped on the basis of the flow of "Ki" in the Keiraku. Although the "Keiraku" has not necessarily been clearly explained in terms of modern medicine, its relations with autonomic nerves and the transmission mechanism of body fluids are now being earnestly studied.

The aforementioned measuring method on the basis of the transient characteristic parameters in the prior-art system is a new departure from the theory that had been widely believed in dermato-electrophysiology that the corium has no relations with the electric characteristics of the skin. A large number of dermato-electrophysiologic studies have been made public and several equivalent circuits corresponding to the characteristics of the skin have been proposed on the basis of experiments. However, the fact is that these equivalent circuits do not coincide with each other, and as a result, no clear-cut conclusion has been reached as to the correlationship between these equivalent circuits and the microscopic structure of the skin. This is because the skin of a living body is of a very non-linear and active nature and has complex frequency characteristics. That is, the behavior of the skin greatly varies depending on the amplitude, waveform, frequency range of the electrical signal applied.

In this respect, the aforementioned prior-art system succeeded in obtaining measurements in linear ranges where no researchers had realized such measurements by reducing the voltage applied and the duration of voltage application, and this led to a conclusion that overthrew the established theory. The defined four transient characteristic parameters AP, BP, TC and IQ, however, just represent apparent features of the waveforms and are not based on the accurate analysis of the waveforms. That is, in the prior-art system, the purpose of which is limited to the diagnosis of the functions of the Keiraku—internal organ in acupuncture/moxibustion medicine, parameters have been required only to represent the functions of the Keiraku—internal organ, and no accurate analysis in terms of equivalent circuits has been required. Thus, the prior-art system has been limited to an extremely narrow applications, such as the Keiraku diagnosis at the Seiketsu.

In the prior-art system, parameters have not always been determined with high accuracy from current data because current waveforms have not been analyzed. This problem is pronounced particularly with the parameters BP and TC. In the aforementioned U.S. Pat. No. 3,971,366, the parameter BP is substituted by a peak value measured in the peak-hold circuit. Due to the deformation in current waveforms caused by the preamplifier (which is particularly remarkable in the initial stage of current change), however, the peak value tends to be lower than the true BP value. Furthermore, there is another problem of poor accuracy because the BP value is determined with the data obtained at a single point. In another method, the parameter BP is determined by selecting several points in the initial stage of current change, and adjusting these points to a polynomial or an exponential function. Since it is impossible to contain many points in these functions with this method, only the data at two or three points are used to determine the parameter BP. It is impossible therefore to improve measuring accuracy by overcoming random noises. The parameter TC, on the other hand, can be determined by extrapolating the functions obtained as they are. This method of determining the parameter TC, in which the functions determined on the basis of the data at two or three points within a considerably shorter period than the attenuating time of the attenuating function, can result only in low reliability of the results.

In general, it is very important to obtain correct electrical equivalent circuits by analyzing current waveforms. It is only by this method that the relationship between the current waveform parameters or equivalent circuit parameters and the anatomical structure of the skin can be established. Furthermore, it is by this method that changes in the characteristics of the skin detected by electrical measurement can be explained microscopically.

It can be expected that the electrophysiological characteristics exhibited by the surface of a living body may vary with different locations on the surface of the living body. Consequently, if a correct analysis method in terms of equivalent circuits can be established correspondingly to the structure of the skin, such an analysis method can be readily applied to any given locations on the surface of the human body.

Having a complicated structure, the skin naturally must have complicated frequency characteristics, an impedance analysis using a sine wave of a single frequency cannot be a correct method. In this respect, using a rectangular-wave pulse having a short rise time, as in the prior-art system, would be far more advantageous than an analysis using sine waves because such pulse signals have a very wide Fourier spectrum.

To find a correct equivalent circuit of the skin not only is electrophysiologically meaningful but also opens up a very wide range of applications. In other words, with such an equivalent circuit, the surface structure of living things, whether animals or plants, can be subjected to electrophysiological analysis. In this way, if a more universal method of electric equivalent circuit analysis that can be applied not only to human beings but also to animals and plants is established, it can be applied to a very wide range of applications, including inspection of the freshness of fruits, monitoring of the growth of agricultural crops.

SUMMARY AND OBJECTS OF THE INVENTION

It is an object of this invention to provide a biological information measuring system that solves the existing problems, realizes measurement of the electrophysiological characteristics of the surface of a living body, and has a wide range of applications.

The present inventors applied a rectangular-wave voltage of a magnitude of 0.5–3 V and a width of 1/1,000 sec across an indifferent electrode provided on part (on the rear sides of both wrists, unless otherwise specified) of the body of a subject and a different electrode brought in contact with a given region being measured. The inventors then measured an electric current I (t) flowing during voltage application to investigate in detail the phenomenon forming the basis of the prior-art system. A detailed analysis of the current waveforms revealed that the measured current waveforms can be approximated with extremely high accuracy over an entire range of 0–1/1,000 sec by an equation expressed by $$I(t) = \sum_{i=1}^{n} I_i^0 e^{-\frac{t}{\tau_i}} + I_{DC} \qquad (1)$$
$$= I_1^0 e^{-\frac{t}{\tau_1}} + I_2^0 e^{-\frac{t}{\tau_2}} + I_3^0 e^{-\frac{t}{\tau_3}} + \ldots + I_{DC}$$
$$= I_1 + I_2 + I_3 + \ldots + I_{DC}$$

where $\tau_1 < \tau_2 < \tau_3 < \ldots$

Equation (1) can be approximated by Equation (1') by discarding the exponential functional components in the fourth and subsequent terms.

$$I(t) = I_1^0 e^{-\frac{t}{\tau_1}} - I_2^0 e^{-\frac{t}{\tau_2}} + I_3^0 e^{-\frac{t}{\tau_3}} + I_{DC} \qquad (1')$$
$$= I_1 + I_2 + I_3 + I_{DC}$$

Equation (1') is schematically represented as shown in FIG. 2. That is, $I_1$–$I_3$ in FIG. 2 represent exponential functional components, $I_{DC}$ a d-c component, respectively. I(t) is the current waveform approximated by the sum of these exponential functional components $I_1$, $I_2$ and $I_3$ and the d-c component $I_{DC}$.

It has been made clear that the above equations can very faithfully reproduce the measured current waveforms in a given region of the entire body surface, including the head, face, back, waist, and limbs.

With the surface of a living body under the normal condition, those exponential functional components in the first and second terms of Equation (1') are major components, with the exponential functional component in the third term being almost negligible. It has been ascertained that the exponential functional component in the third term emerges clearly as the keratinized layer of the epidermis is removed.

The equivalent circuit of Equation (1) is shown in FIG. 3. That is, the equivalent circuit comprises a parallel circuit consisting of a plurality of series circuits of resistors $R_1$, $R_2$, $R_3$, - - -, and capacitors $C_1$, $C_2$, $C_3$, - - -, and a resistor $R_{DC}$. This parallel circuit is connected to a d-c power-supply 140 via a switch 130 so that a rectangular-wave pulse voltage is applied to the parallel circuit as the switch 130 instantaneously closes. The equivalent circuit parameters $R_i$, $R_{DC}$, $C_i$ as parameters of the resistance and capacitance of the equivalent circuit and the current waveform parameters in Equation (1) have the following relationship:

$$R_i = \frac{V}{I_i} \quad (2)$$

$$R_{DC} = \frac{V}{I_{DC}} \quad (3)$$

$$C_i = \frac{I_i \tau_i}{V} \quad (4)$$

where V is a voltage value of the d-c power supply 140, $I_i$ is a current flowing in the series circuit of the resistor $R_i$ and the capacitor $C_i$, $I_{DC}$ is a current flowing in the resistor $R_{DC}$, $\tau_i = R_i C_i$, i=1, 2, 3, - - -.

It is expected that the equivalent circuit described above has a good correspondence with the anatomical structure of the skin.

The relationship between the transient characteristic parameters defined in the prior-art system (BP, AP, IQ, TC), and the current waveform parameters and the equivalent circuit parameters in this invention is expressed by the following equation.

$$BP = \sum_{i=1}^{n} I_i^0 + I_{DC} = V \left( \sum_{i=1}^{n} \frac{1}{R_i} + \frac{1}{R_{DC}} \right) \quad (5)$$

$$AP = I_{DC} = \frac{V}{R_{DC}} \quad (6)$$

$$IQ = \sum_{i=1}^{n} \tau_i I_i^0 = V \sum_{i=1}^{n} C_1 \quad (7)$$

$$TC = \frac{\sum_{i=1}^{n} I_i^0}{\sum_{i=1}^{n} \frac{I_i^0}{\tau_1}} = \frac{\sum_{i=1}^{n} \frac{1}{R_i}}{\sum_{i=1}^{n} \frac{1}{C_i R_i^2}} \quad (8)$$

Consequently, the parameters BP, AP, IQ and TC defined in the prior-art system can be obtained in the system of this invention.

Advantages of the system of this invention are as follows. In this invention, the functions in Equation (1) can be adjusted to measured data using a method, which will be described later. With this method, possible deviation between Equation (1) and measured data can be minimized by using all the measured data in principle (1,000 pieces of data if measurement is made in 1 μsec increments from 0 to 1 msec, for example) to determine the current waveform parameters. As noted earlier, BP and TC among the parameters BP, AP, TC and IQ cannot necessarily be obtained with high accuracy with the prior-art system. In this invention, on the other hand, the aforementioned disadvantages with the prior-art system can be substantially improved since the four parameters of BP, AP, TC and IQ can be determined using Equations (5)-(8) on the basis of the current waveform parameters determined with high accuracy, as mentioned above.

As noted above, the system of this invention can determine the equivalent circuit parameters from the current waveform parameters using Equations (2)-(4). These equivalent circuit parameters are naturally affected by the physiological or pathological state of the skin. Changes in blood stream and blood volume in the capillary blood vessels developing in the corium, the ionic composition of body fluid, body surface temperature, the degree of tension of autonomic nerves, for example, appear as changes in the constants of the equivalent circuit parameters.

The skin and the subcutaneous tissue are immunologically important as barriers against the attack by external etiologies, and at the same time, are locations where any disturbance of an internal organ appears in the form of tension in the tissue through a so-called viscerosensory reflex. Consequently, the application of the system of this invention to diagnosis is not necessarily limited to the field of acupuncture/moxibustion medicine, but the system of this invention has a wide range of applications in terms of modern medicine.

The biological information measuring system of this invention can achieve the following effects.

(1) Whereas it has been difficult with the prior-art system to obtain accurate values of the parameters BP and TC, this invention, in which the parameters BP and TC are calculated on the basis of the current waveform parameters, can obtain more accurate values.

(2) This invention, in which not only the transient characteristic parameters AP, BP, TC and IQ obtained by calculating the current waveform parameters, but also the current waveform parameters $I_i^0$, $\tau_i$, and $I_{DC}$ and/or the equivalent circuit parameters $R_i$, $C_i$ and $R_{DC}$ are used, can obtain much more and more accurate biological information. Particularly, as to the current waveform parameters, accurate biological information can be obtained by using $I_1^0$, $I_2^0$, $\tau_1$, $\tau_2$, and $I_{DC}$ as the current waveform parameters because measured current waveforms can be very accurately approximated with the exponential functional components up to the third terms and the d-c component. In addition, as to the equivalent circuit parameters, the parameter $R_1$ is a resistance distributing along a current path between electrodes, while the parameters $R_2$ and $R_3$ can be interpreted as indicating that they are determined by the nature of the skin immediately below the different electrode and the state of interface between the electrode and the skin. In this way, the equivalent circuit parameters have a potential of adding new knowledge to the field of electrophysiological study in the vicinity of the surface of a living body.

Diagnosis can be performed by arbitrarily combining these transient characteristic parameters, current waveform parameters and equivalent circuit parameters. Using the transient characteristic parameters AP and BP, and the equivalent circuit parameters $R_1$ and $R_2$, diagnosis of the pathological state of a living body can be performed.

(3) According to this invention, the original transient characteristic parameters can be reproduced from the current waveform parameters. So, the transient current itself does not have to be stored, and only the current waveform parameters are needed to be stored. This leads to a small storage capacity of memory devices, such as magnetic disc units.

(4) By using the current waveform parameters and/or the equivalent circuit parameters as biological information, the accuracy of detecting abnormality of a living body is improved with this invention, compared with the prior-art system. That is, the four parameters AP, BP, TC and IQ are effective in the Keiraku diagnosis, but these parameters are not independent from each other, and the current waveform parameters or the equivalent circuit parameters ($R_1$, $R_2$, $C_1$, $C_2$, $R_{DC}$) have rather a clear electrical characteristics. This means that by using the current waveform parameters or the equivalent circuit parameters, more detailed diagnosis with a larger volume of information is made possible. For example, the pathological state of a living body can be diagnosed from the $R_1$—$C_1$ plot of the equivalent circuit parameters, and the disturbance of the dorsal spine can be diagnosed from the $R_1$—$C_1$ plot and the $R_2$—$C_2$ plot, with the dorsal "Yuketsu" used as the diagnostic point.

(5) Particularly, the graphic processing of parameter distribution using the mapping arithmetic section has made it possible to detect more complicated abnormality of a living body.

(6) Since the biological information measuring system of this invention can selectively detect as biological information the transient characteristic parameters, the current waveform parameters and the equivalent circuit parameters, various diagnoses, such as those of the pathological state of a subject who has an indefinite complaint or pains at various locations of the body, the malocclusion of teeth, and the distorted spine, can be carried out.

(7) The system of this invention can detect biological information not only of human beings but also of animals and plants, and has a wide range of applications.

BRIEF DESCRIPTION OF THE DRAWINGS

FIG. 17 is a diagram of assistance in explaining the measuring principle of the distorted spine.

DETAILED DESCRIPTION OF THE PREFERRED EMBODIMENT

EMBODIMENT 1

Figure 4:
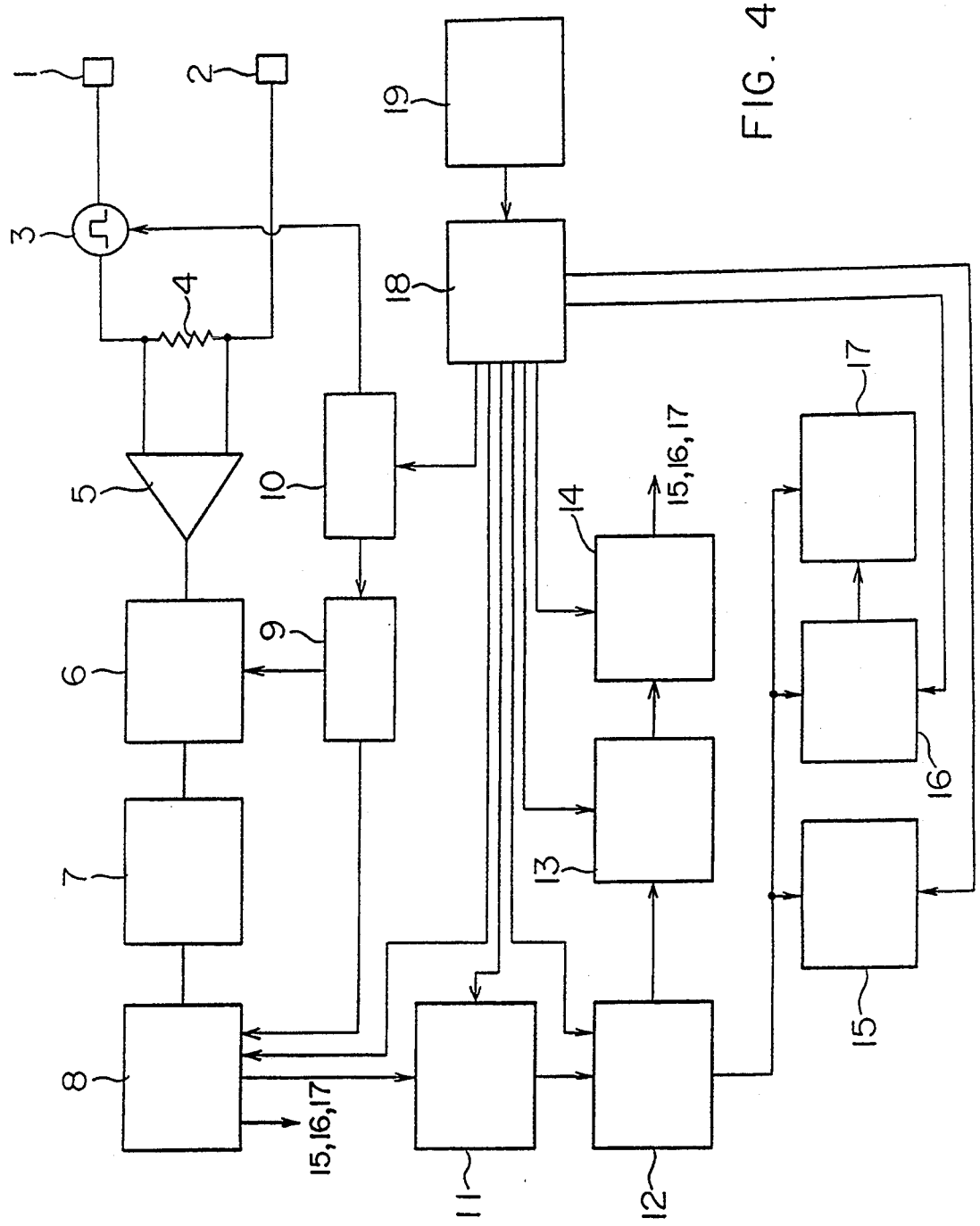
FIG. 4 is a block diagram illustrating the first embodiment of this invention.

FIG. 4 is a block diagram of the first embodiment of the biological information measuring system of this invention. This biological information measuring system comprises a different electrode 1 and an indifferent electrode 2 forming a pair of electrodes attached to a living body; a rectangular voltage pulse source 3 for applying a one-shot rectangular voltage pulse across these electrodes 1 and 2; a current detecting resistor 4 for detecting a current flowing in a living body as the rectangular voltage pulse is applied; a pre-amplifier 5 for amplifying the detected current; a sampling circuit 6 for sampling the amplified current; an analog-digital (A/D) converter 7 for converting analog sampling values to digital values; a multi-channel waveform memory 8 for storing digital values in a time series; a clock generating circuit 9 for generating a clock signal as the time base for the sampling circuit 6 and the waveform memory 8; a start-signal generator 10 for generating start signals that cause the rectangular voltage pulse source 3 and the clock generating circuit 9 to start; a waveform analyzing section 11 that analyzes the current in the form of the sum of a plurality of exponential functional components and a single d-c component on the basis of the waveform data read from the waveform memory 8; a waveform parameter memory 12 for storing the current waveform parameters obtained; a waveform synthesizing section 13 for calculating the exponential functional components and the d-c component from the current waveform parameters read out from the waveform parameter memory 12 to calculate the sum thereof; a synthesized waveform memory 14 for storing the synthesized waveform; a magnetic disc unit 15 for storing the data located in the memories 8, 12 and 14 onto a magnetic disc; a CRT display 16 for displaying data; a printer 17 for printing data; an instruction execution arithmetic section 18 for controlling the above sections; and an instruction input section 19 for inputting an instruction.

The operation of this embodiment will be described on the basis of the following measurement cases.

(Measurement Case 1)

First, the different electrode 1 is attached to the tip of the thumb of the left had of an adult male, and the indifferent electrode 2 to the wrist. Next, an instruction is keyed in directly from the keyboard, or a instruction stored in advance in the form of software for data integration and analysis in the magnetic disc unit 15 is called and sent to the instruction execution arithmetic section 18. The instruction execution arithmetic section 18 drives the start-signal generator 10 to generate a start pulse, which in turn is sent to the rectangular voltage pulse source 3 and the clock generating circuit 9.

The rectangular voltage pulse source 3, when driven by the start pulse, generates and applies a constant-voltage pulse of 3 V and a duration of 1/1,000 sec across the different electrode 1 and the indifferent electrode 2. This causes a transient current to flow across the different and indifferent electrodes 1 and 2. The current is detected by the current detecting resistor 4, amplified by the pre-amplifier 5, and then sampled at every microsecond in the sampling circuit 6. The sampled value is converted to a digital value in the A/D converter 7, and stored in time-series in the waveform memory 8, which is a multi-channel memory.

Table 1 shows the current values (µA) at every microsecond from 0 to 45 µsec. The contents of Table 1 may be displayed on the CRT display 16, or printed out by the printer 17. The table is stored in the magnetic disc unit 15. Each row of horizontal boxes in the table containing the value of the current at adjacent 1 µsec intervals. Each row contains 10 boxes and the right end of one row is continued at the left end of the next row down. The left most box indicating the time point at which the row starts. The upper most row indicating the number of 1 µsec intervals from the time point on the left.

TABLE 1

|  | µ sec | | | | | | | | | | (µA) |
|---|---|---|---|---|---|---|---|---|---|---|
|  | 0 | 1 | 2 | 3 | 4 | 5 | 6 | 7 | 8 | 9 |
| 0µ sec mark | — | 2794 | 2090 | 1591 | 1246 | 1010 | 827 | 700 | 591 | 517 |
| 10µ sec mark | 447 | 397 | 348 | 320 | 294 | 267 | 239 | 225 | 204 | 200 |
| 20µ sec mark | 183 | 176 | 158 | 161 | 147 | 144 | 130 | 133 | 123 | 123 |
| 30µ sec mark | 116 | 116 | 109 | 109 | 102 | 105 | 98 | 98 | 95 | 102 |
| 40µ sec mark | 91 | 95 | 88 | 88 | 80 | 88 | | | | |

The waveform analyzing section 11 reads the current values in Table 1 from the memory 8 and analyzes them to obtain the current waveform parameters. In this example, the waveform analyzing section 11 obtains the current waveform parameters $I_1^0$, $I_2^0$, $\tau_1$, $\tau_2$, and $I_{DC}$ in the current approximate equation given below using the method of non-linear least square.

$$I = I_1^0 e^{-\frac{t}{\tau_1}} + I_2^0 e^{-\frac{t}{\tau_2}} + I_{DC} \tag{9}$$

The resulting current waveform parameters are stored in the waveform parameter memory 12. Table 2 shows the resulting current waveform parameters. The contents of Table 2 may be displayed on the CRT display 16, or outputted by the printer 17. The table is stored in the magnetic disc unit 15.

TABLE 2

| $I_1^0$ | $\tau_1$ | $I_2^0$ | $\tau_z$ | $I_{DC}$ |
|---|---|---|---|---|
| 2730 µA | 2.5µ sec | 930 µA | 9.0µ sec | 92 µA |

The waveform synthesizing section 13 reads the current waveform parameters $I_1^0$, $\tau_1$, $I_2^0$, $\tau_2$, and $I_{DC}$, calculates the exponential functional components $$I_1^0 e^{-\frac{t}{\tau_1}}, I_2^0 e^{-\frac{t}{\tau_2}}$$

and the d-c component $I_{DC}$, calculates the sum thereof to synthesize a current waveform. The synthesized current waveform is stored in the synthesized waveform memory 14.

The synthesized current waveform data stored in the synthesized waveform memory 14 is given in Table 3. The contents of Table 3 may be displayed on the CRT display 16, or outputted by the printer 17, and is stored in the magnetic disc unit 15. This synthesized current waveform data represents current values at every microsecond from 0 to 45 microseconds of the synthesized current waveform.

TABLE 3

|  | µ sec | | | | | | | | | | (µA) |
|---|---|---|---|---|---|---|---|---|---|---|
|  | 0 | 1 | 2 | 3 | 4 | 5 | 6 | 7 | 8 | 9 |
| 0µ sec mark | 3752 | 2754 | 2063 | 1580 | 1239 | 995 | 817 | 685 | 585 | 508 |
| 10µ sec mark | 448 | 399 | 359 | 311 | 290 | 274 | 253 | 235 | 219 | 204 |
| 20µ sec mark | 192 | 182 | 172 | 164 | 156 | 149 | 143 | 138 | 133 | 129 |
| 30µ sec mark | 125 | 121 | 118 | 115 | 113 | 111 | 109 | 107 | 105 | 104 |
| 40µ sec mark | 102 | 101 | 100 | 99 | 99 | 98 | | | | |

Figure 5:
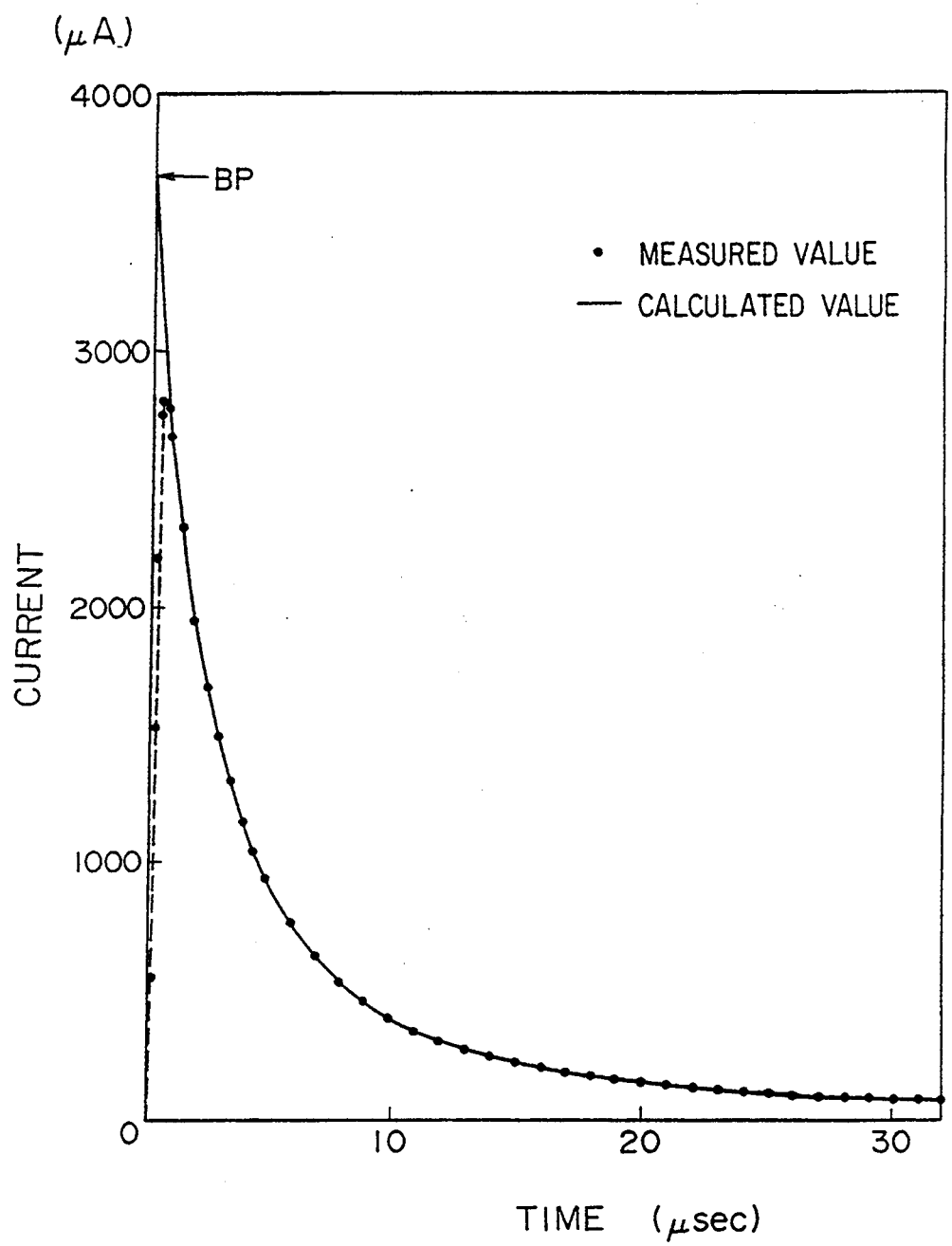
FIG. 5 is a diagram illustrating a current waveform reproduced on the basis of current waveform parameters.

This waveform analysis reveals that a waveform is successfully reproduced with two exponential functional components and a d-c component. This is shown in FIG. 5. Black dots represent measured values in Table 1, a solid line represents the current waveform reproduced on the basis of calculated values in Table 3. This reproduced current waveform may be displayed on the CRT display 16, or outputted by the printer 17.

This embodiment makes it possible to use current waveform parameters, reproduced current waveform data or reproduced current waveforms as biological information. Particularly, the reproduced current waveforms lend themselves to quick visual identification of information.

In terms of a diagnosis system or an electrophysiological measuring system, current waveforms should preferably be such that all the information contained in the current waveforms be collected and stored in a memory. This is because current waveforms themselves are instrumental to quick visual identification of information. If a current waveform itself is to be stored, it is necessary to measure 100 μsec–1 msec at a time resolution of 1 μsec, min. to reproduce the current waveform. That is, 100 to 1,000 pieces of three- to four-digit values have to be stored. The system of this embodiment is capable of completely reproducing current waveforms with the sum of two exponential functional components $$I_1^0 e^{-\frac{t}{\tau 1}}, I_2^0 e^{-\frac{t}{\tau 2}}$$

and a d-c component $I_{DC}$. This means that storing five sets of current waveform parameters $I_1^0$, $\tau_1$, $I_2^0$, $\tau_2$, $I_{DC}$ in the magnetic disc unit 15, instead of storing the current waveforms themselves, will suffice for the purpose. That is, the capacity of the magnetic disc unit 15 necessary to store data can be reduced by a factor of 1/20–1/200.

(Measurement Case 2)

An example to which the system of this embodiment was applied to the study of the electrophysiological structure of the skin is shown here. The indifferent electrode 2 was attached to a location slightly above the heads of the ulnas outside both wrists, and the measuring position was set at a region in the vicinity of the central part of the inside of a left forearm. The different electrode 1 as a gel electrode 10 mm in diameter was attached at this measuring position. A pulse voltage of 3 V, 1/1,000 sec was applied from the rectangular voltage pulse source 3, and the resulting current was sampled every 1 μsec with the sampling circuit 6, A/D-converted with the A/D converter circuit 7, and stored in the waveform memory 8. After a waveform analysis in the waveform analyzing section 11, the waveform parameter memory 12 and the waveform synthesizing section 13 to obtain three exponential functional components $$I_1^0 e^{-\frac{t}{\tau 1}}, I_2^0 e^{-\frac{t}{\tau 2}}, I_3^0 e^{-\frac{t}{\tau 3}}$$

and a d-c component $I_{DC}$. The exponential functional component in the third term, however, was negligibly small, compared with the other two components. Next, in order to make clear which layer of the skin contributes to determining these current components, measurement was made by following the procedures of removing the gel electrode 1, applying cellophane adhesive tape to the skin, stripping the tape to strip part of the keratinized layer from the skin surface, and then replacing the gel electrode 1. The current waveform parameters obtained by analyzing the current values measured after the removal of the keratinized layer with cellophane adhesive tape was conducted 11 times are given in Table 4.

TABLE 4

| $I_1^0$ | $\tau_1$ | $I_2^0$ | $\tau_z$ | $I_3^0$ | $\tau_3$ |
|---|---|---|---|---|---|
| 3600 μA | 1.75μ sec | 2050 μA | 8.0μ sec | 415 μA | 48.5μ sec |

Although no clear conclusion can be derived from these measurement results, more detailed experiments in this direction could lead to new knowledge on the electrophysiological structure of the skin.

(Measurement Case 3)

Figure 6:
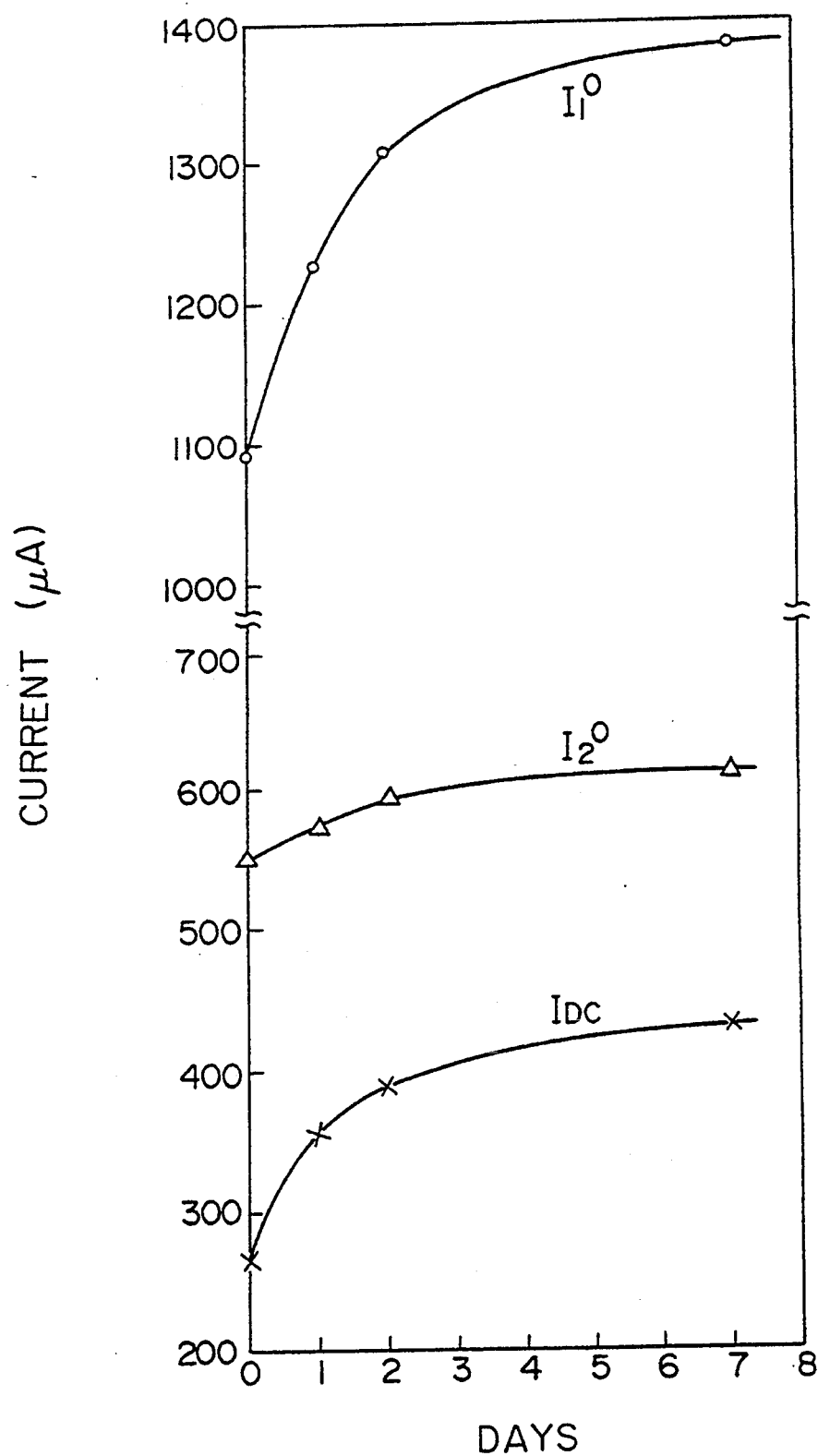
FIG. 6 is a graph illustrating secular changes in current waveform parameters.

An example where the current waveform analysis using the system of this embodiment was applied to plants is shown here. In the experiment, an orange was used. Using gel electrodes used for electrocardiogram, the different electrode 1 and the indifferent electrode 2 were provided on the surface of a fresh orange purchased at a fruit shop. Changes with time in the current waveform parameters $I_1^0$, $I_2^0$, and $I_{DC}$ obtained by carrying out measurements across the electrodes, with the orange allowed to stand in the room, and subjecting the measurement results to waveform analysis with the waveform analyzing section 11 are shown in FIG. 6. The current waveform parameters $I_1^0$ and $I_{DC}$ apparently increases rapidly as days go by, then gradually levels off, and eventually the changes are almost saturated in a week. Changes in $I_2^0$, on the other hand, are relatively small. The results of this measurement case seem to point to the potential of applying the system of this embodiment to the measurement of the freshness of fruits.

EMBODIMENT 2

Figure 1:
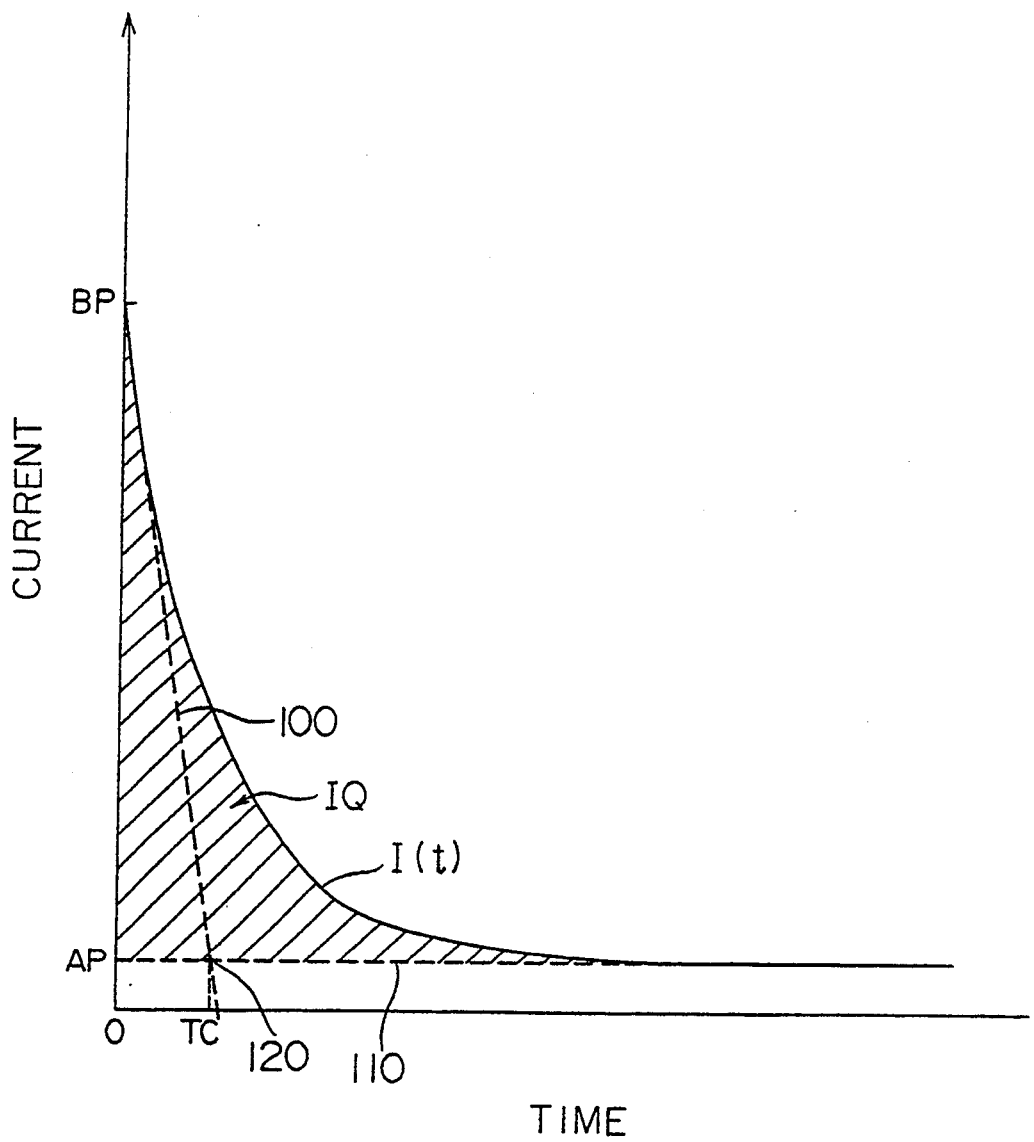
FIG. 1 is a waveform diagram of assistance in explaining transient characteristic parameters.
Figure 2:
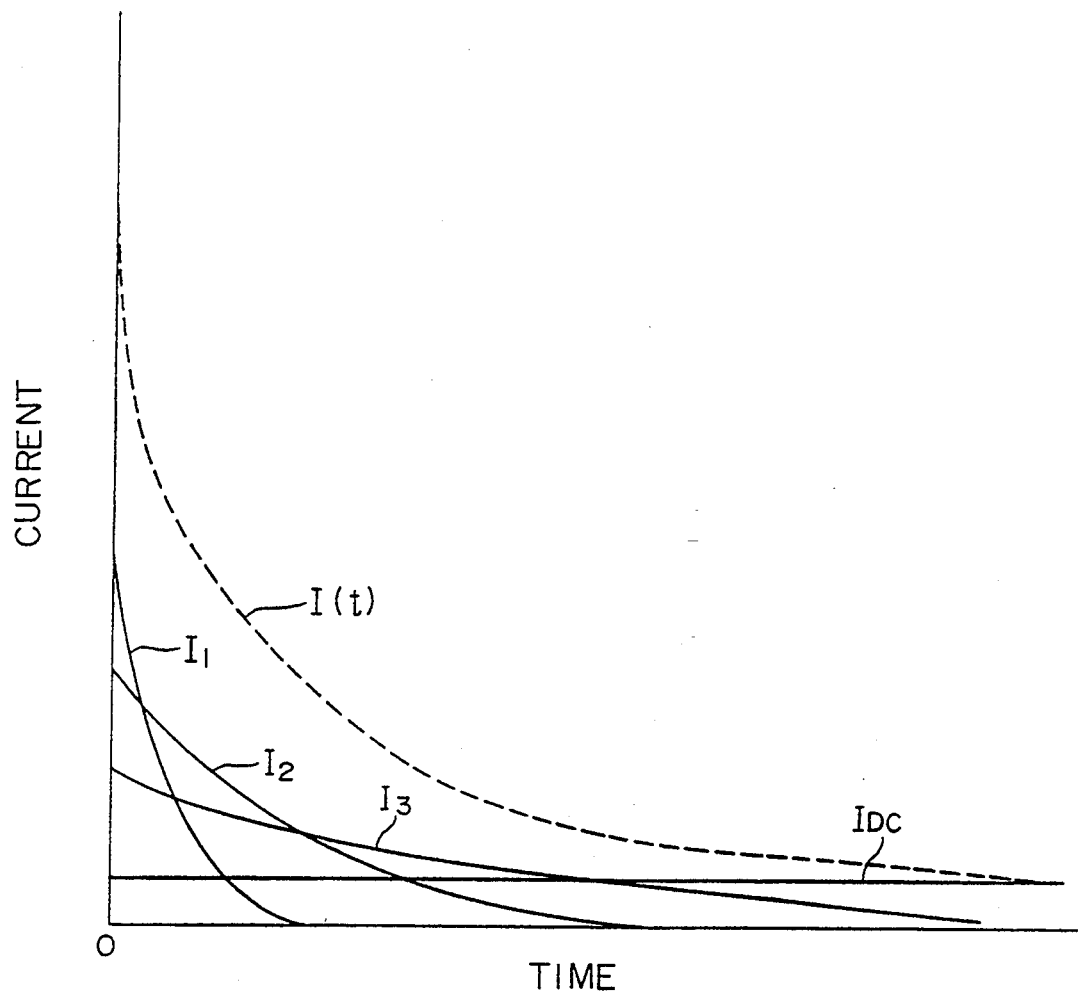
FIG. 2 is a diagram illustrating transient current components and a d-c component.
Figure 3:
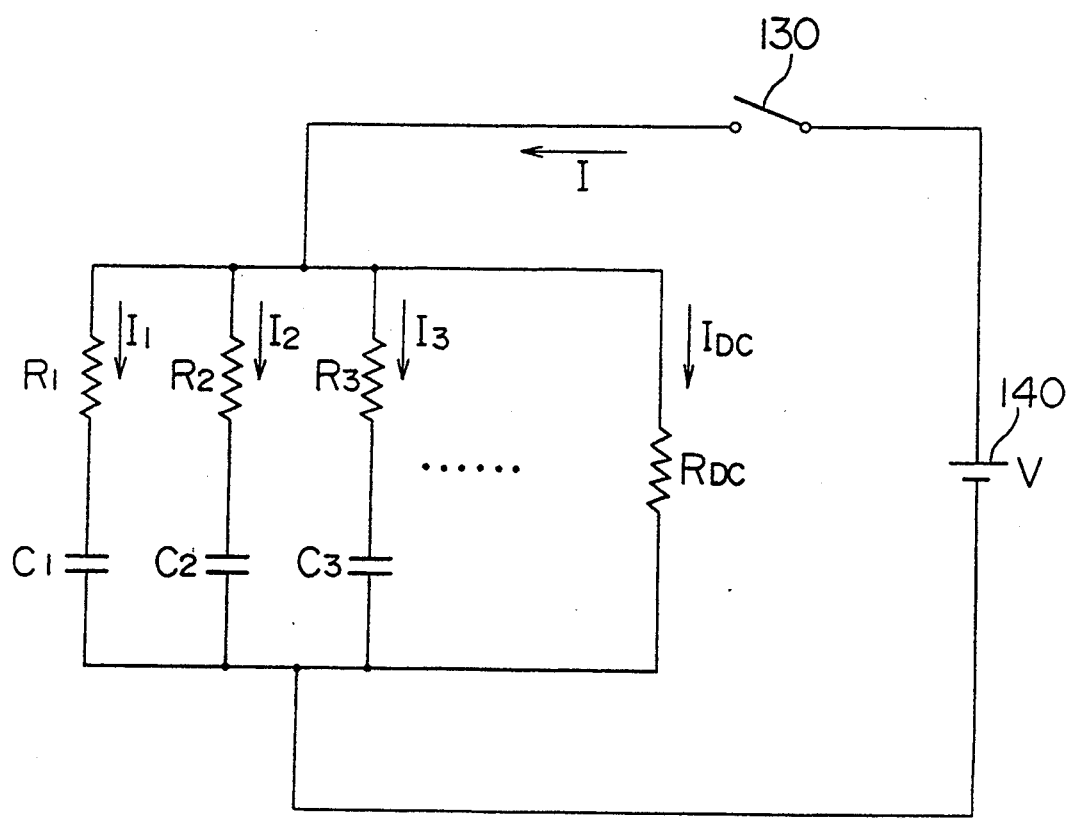
FIG. 3 is a diagram illustrating an equivalent circuit.
Figure 7:
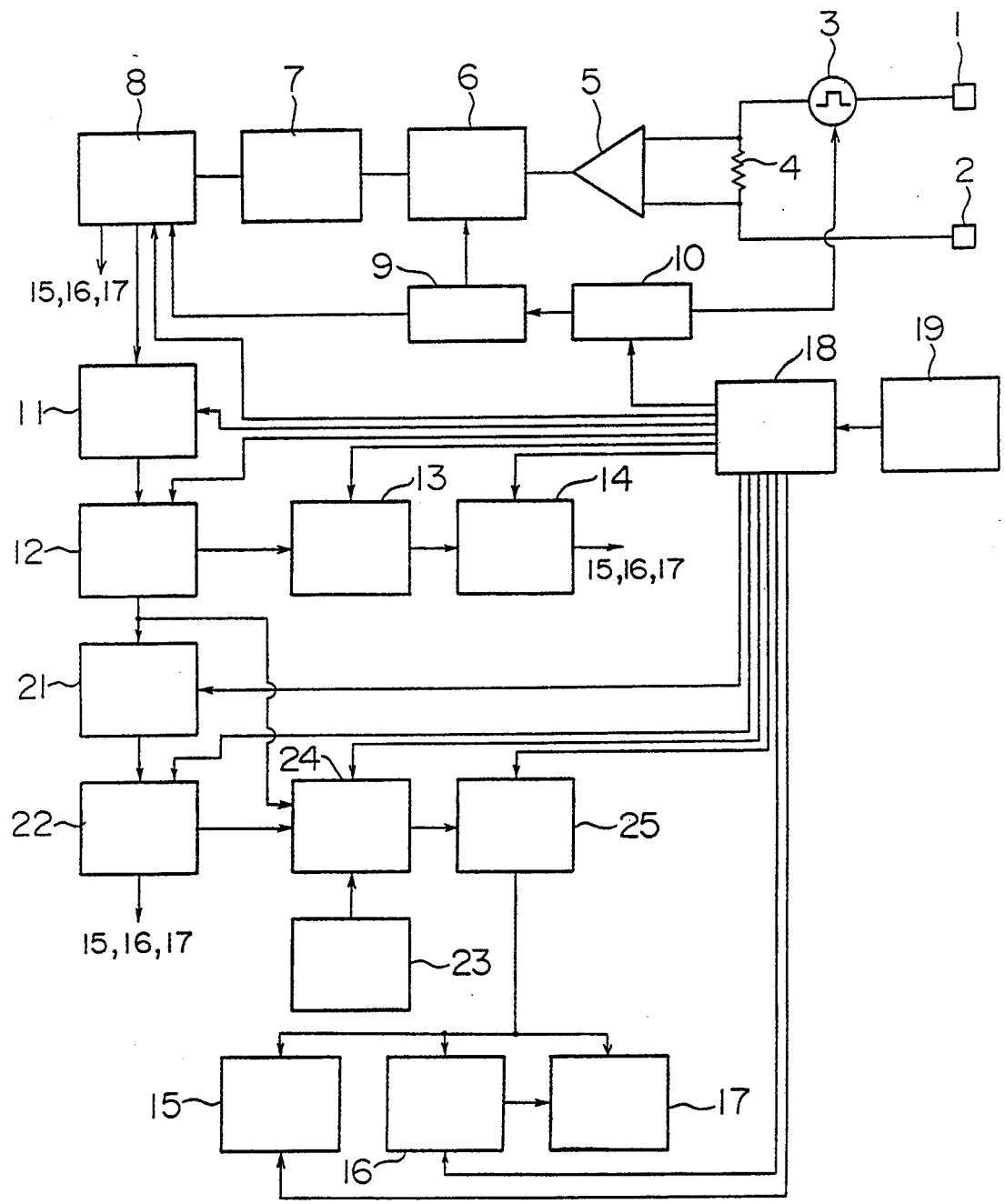
FIG. 7 is a block diagram illustrating the second embodiment of this invention.
Figure 8:
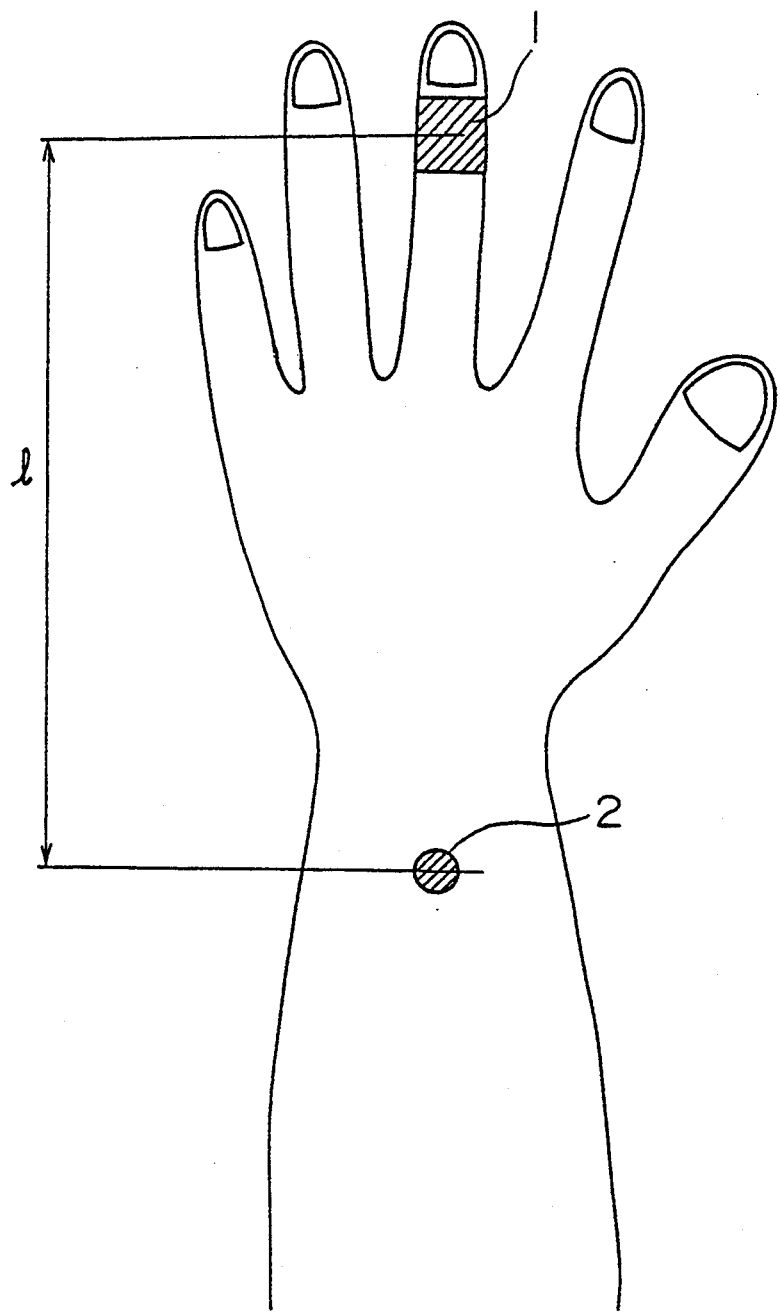
FIG. 8 is a diagram illustrating the positions of the body to which electrodes are attached.

FIG. 7 is a block diagram of the second embodiment of the biological information measuring system according to this invention. This embodiment comprises the biological information measuring system shown in FIG. 1; a diagnosis parameter arithmetic section 21 for calculating parameters required for diagnosis, including equivalent circuit parameters, transient characteristic parameters AP, BP, TC and IQ on the basis of current waveform parameters; a diagnosis parameter memory 22 for storing the calculated diagnosis parameters; a diagnosis standard input section 23; a diagnosis arithmetic section 24 for comparing the current waveform parameters from the waveform parameter memory 12, the diagnosis parameters from the diagnosis parameter memory 22 with the standard values inputted from the diagnosis standard input section 23, or classifying the patterns of the correlationship among the parameters, identifying the difference between the left and right of parameters of the same type and different measuring positions, identifying the difference between hands and feet, comparing the size of average values, or detecting deviations of the parameters of a living body from various laws, and integrating and compiling these results to make diagnosis; and a diagnosis result memory 25.

As the standard values inputted from the diagnosis standard input section 23, the average values of current waveform parameters, equivalent circuit parameters and transient characteristic parameters at a plurality of measuring positions of a living body, or the average values of current waveform parameters, equivalent circuit parameters and transient characteristic parameters obtained by statistically processing measurement results on a normal living body can be used.

The operation of this embodiment will be described on the basis of the following measurement cases.

(Measurement Case 4)

The different electrode (diameter: 6 mm) 1 is attached to what acupuncture/moxibustion medicine calls "Shoshoketsu") of the third finger of the left hand. A 20 mm×35 mm cardiogram electrode is used as the indifferent electrode 2. Current measurement is carried out by changing the position of the indifferent electrode 2, and the measurement results are stored in the waveform memory 8. The waveform analyzing section 11 analyzes the measurement data read from the waveform memory 8, obtain current waveform parameters to store in the waveform parameter memory 12.

The diagnosis parameter arithmetic section 21 reads current waveform parameters from the waveform parameter memory 12, and calculates equivalent circuit parameters using Equations (2)–(4). The calculated equivalent circuit parameters are stored in the diagnosis parameter memory 22.

Figure 9A:
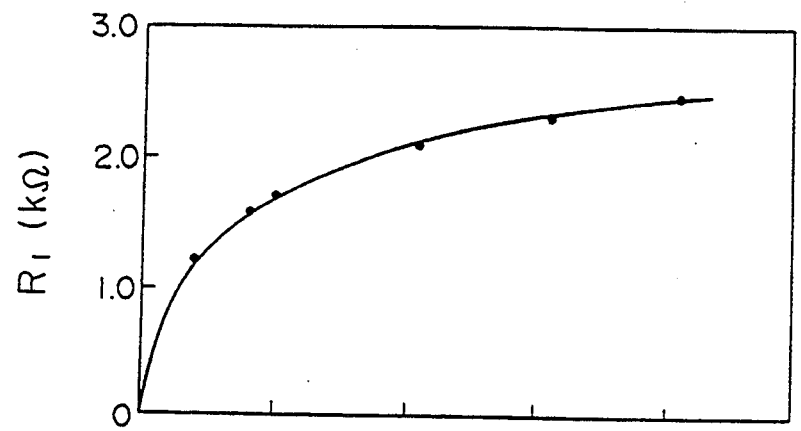
FIGS. 9a, 9b, and 9c are graphs illustrating the dependence of the equivalent circuit parameter $R_i$ on the distance between electrodes.
Figure 9B:
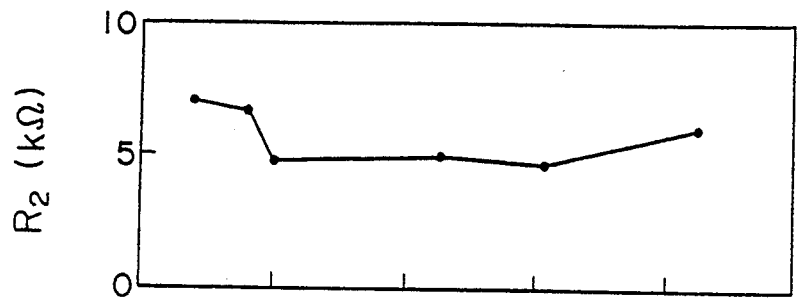
Figure 9C:
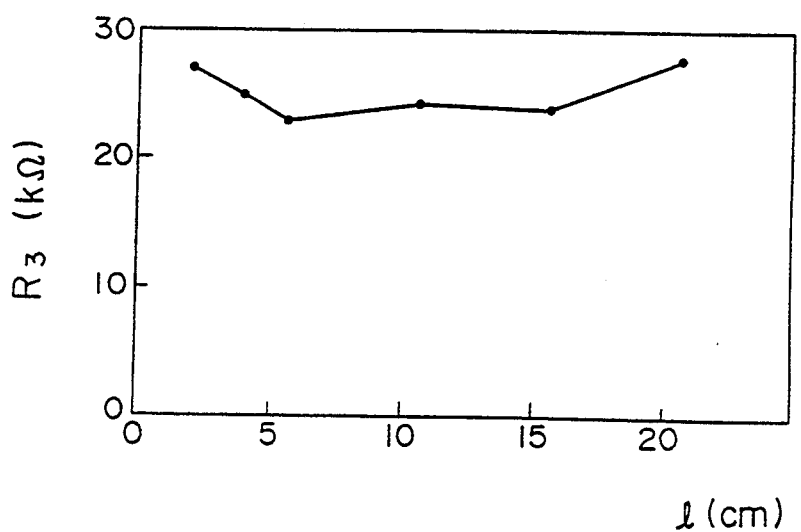

Measurement is carried out by changing the distance 1 between the different electrode 1 and the indifferent electrode 2 to determine the dependence of the equivalent circuit parameters $R_1$, $R_2$ and $R_3$ on the distance between the different and indifferent electrodes. FIG. 9 is a graphic representation of the measurement results.

As shown in Graph (a), the parameter $R_1$ shows a pronounced non-linear dependence on the distance 1 (cm) between the electrodes. The parameters $R_2$ and $R_3$, on the other hand, do not show any clear distance-dependence, as shown in Graphs (b) and (c). This is interpreted as showing that the parameter $R_1$ is a resistance distributing along the current path between the electrodes, while the parameters $R_2$ and $R_3$ are determined by the nature of the skin immediately below the different electrode 1 and the state of interface between the electrodes and the skin. The electrical nature of the surface of a living body has heretofore been considered to be determined by the area immediately below the different electrode, and the fact that it is dependent on the length of the current path was not known. In this way, the system of this invention has the potential of adding new knowledge to the field of electrophysiological research in the vicinity of the surface of a living body.

(Measurement Case 5)

In this measurement case, too, five current waveform parameters $I_1^0$, $\tau_1$, $I_2^0$, $\tau_2$, and $I_{DC}$ as approximate waveforms are determined with the non-linear least square method by taking advantage of the fact that a current waveform can be approximated with high accuracy by the sum of two exponential functional components and a d-c component over the entire region being measured.

The diagnosis parameter arithmetic section 21 reads five current waveform parameters from the waveform parameter memory 12 and calculates transient characteristic parameters AP, BP, TC and IQ using Equations (5)–(8). These parameters are stored in the diagnosis parameter memory 22. The diagnosis parameters can be displayed on the CRT display 16, or outputted by the printer 17. They are stored in the magnetic disc unit 15.

The parameter BP and TC values obtained from ten current measurements each measured at the same point (the left "Shoshoketsu") by the prior-art diagnosis system and the biological information measuring system of this embodiment, and the average values and standard deviations thereof are given in Table 5 to compare the measurement results by the prior-art system with those by the biological information measuring system of this embodiment. The table indicates that the values determined by the system of this invention show high accuracy. In Table 5, the linear approximation represents the measurement results by the prior-art diagnosis system, and the 2-exponential function approximation represents the measurement results by the biological information measuring system of this embodiment.

TABLE 5

| | Linear approximation | 2-exponenntial function approximation |
|---|---|---|
| BP | 3436 μA | 3679 μA |
| $\sigma_{BP}$ | 76 μA | 75 μA |
| $\sigma_{BP}/BP$ | 2.22% | 2.03% |
| TC | 2.98μ sec | 8.42μ sec |
| $\sigma_{TC}$ | 0.12μ sec | 0.3μ sec |
| $\sigma_{TC}/TC$ | 4.03% | 3.60% |

BP, TC: Average value
$\sigma_{BP}$, $\sigma_{TC}$: Standard deviations

The four parameters AP, BP, TC and IQ are effective for the Keiraku diagnosis, but these parameters are not independent from each other, as noted earlier, and the five current waveform parameters ($I_1^0$, $I_2^0$, $\tau_1$, $\tau_2$ and $I_{DC}$) or the equivalent circuit parameters ($R_1$, $R_2$, $C_1$, $C_2$ and $R_{DC}$) have clearer electrical characteristics. Consequently, more detailed diagnosis with a larger volume of information is made possible by using these current waveform parameters or equivalent waveform parameters, as will be shown by other embodiments later.

(Measurement Case 6)

An example of diagnosis where current waveform parameters and equivalent circuit parameters are applied to the measurement of the Keiraku-internal organ functions at the Seiketsu is shown here.

A 64-years-old female who had indefinite complaints and received acupuncture/moxibustion treatments was chosen as a subject. Measurements at the Seiketsu were made on the subject using the system of this embodiment on every treatment day, and the measurement results, the therapist's observations and changes in the subject's subjective symptoms were compared.

Current waveform parameters $I_1^0$, $I_2^0$, $\tau_1$ and $\tau_2$ are used as diagnosis parameters at the Seiketsu for each Keiraku, $C_1$ and $C_2$ are used as equivalent circuit parameters, and AP as transient characteristic parameters. The current waveform parameters are calculated with the waveform analyzing section 11 and stored in the waveform parameter memory 12, while the equivalent circuit parameters and the parameter AP are calculated with the diagnosis parameter arithmetic section 21 and stored in the diagnosis parameter memory 22.

Figure 10:
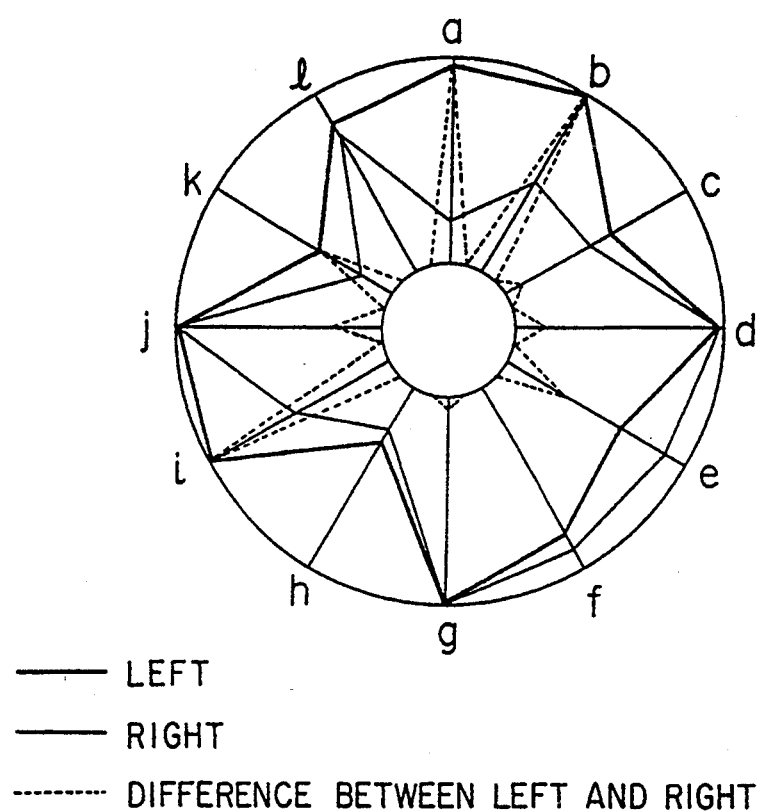
FIG. 10 is a circular graph of parameters.
Figure 11A:
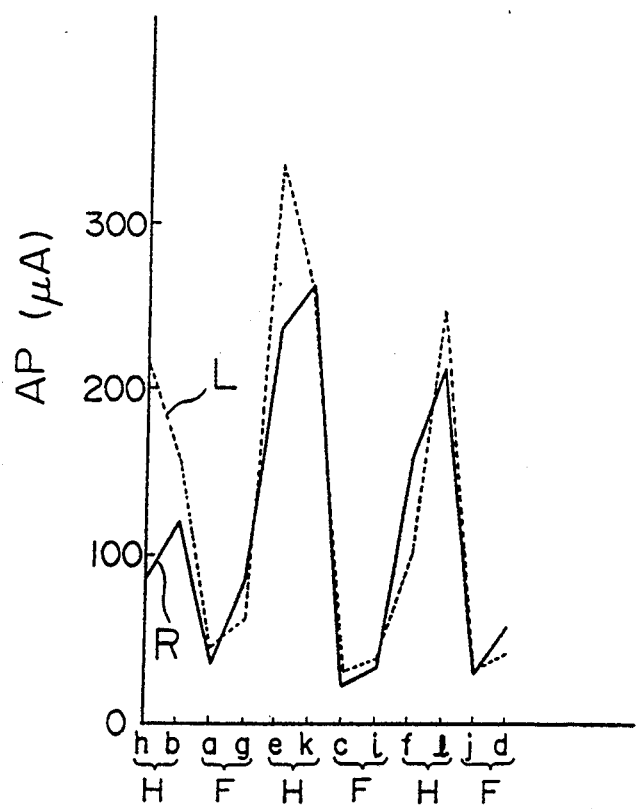
FIGS. 11a-d are broken-line graphs of parameters.
Figure 11C:
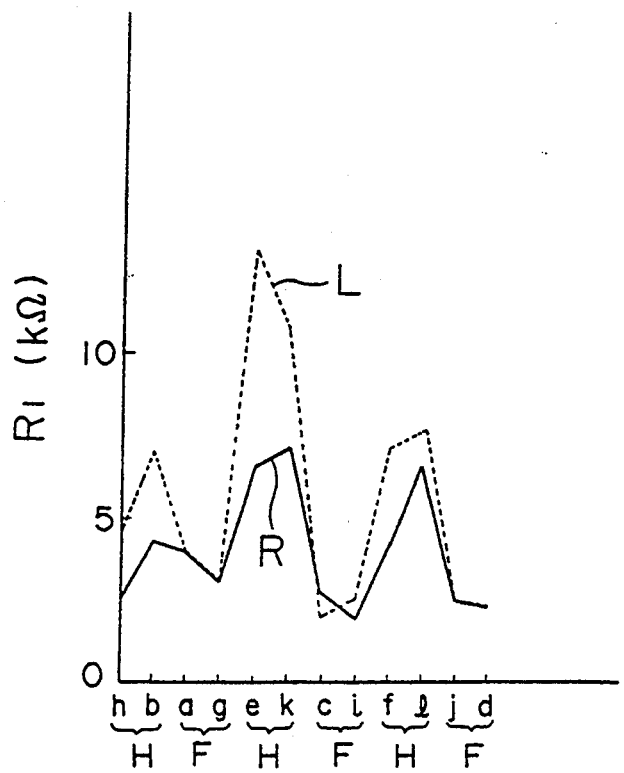
Figure 11B:
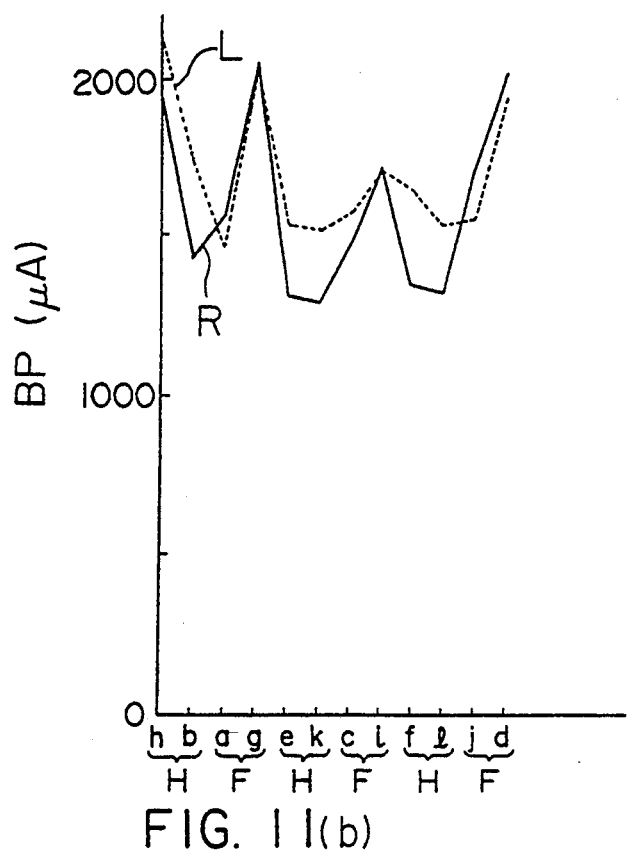
Figure 11D:
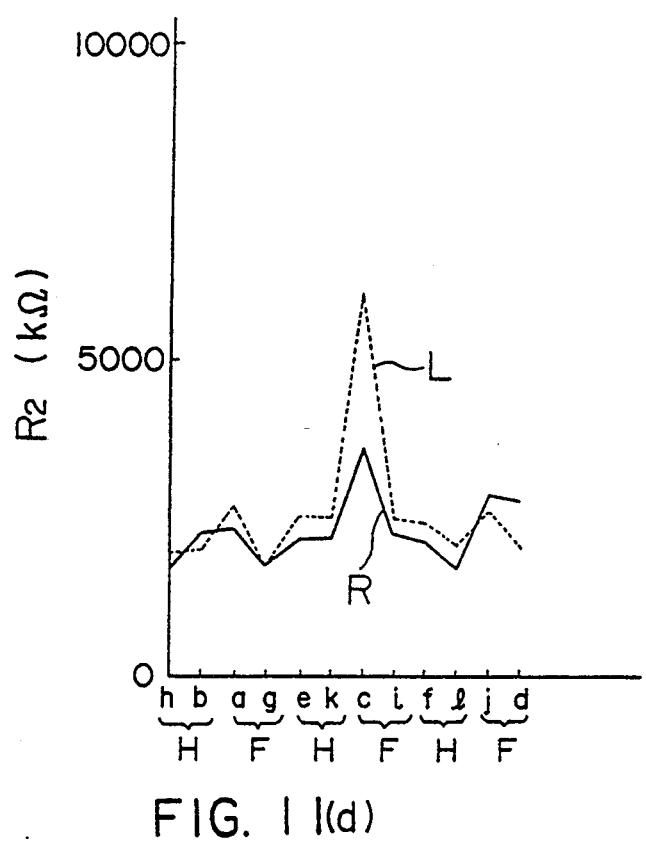

In the diagnosis arithmetic section 24, the current waveform parameters $I_1^0$, $I_2^0$, $\tau_1$ and $\tau_2$ are read from the waveform parameter memory 12, and the equivalent circuit parameters $C_1$ and $C_2$ and the parameter AP are read from the diagnosis parameter memory 22. A circular graph as shown in FIG. 10 is prepared, in which the diagnosis parameters for each Keiraku are plotted so as to represent the left and right of the body, and the difference between the left and right. Then, the calculated data are stored in the diagnosis result memory 25. In the pattern of the circular graph shown in FIG. 10, each of the Keiraku a–l has its own name associated with each organ to which the Keiraku is related. The names of the Keiraku are given below.

a: I-kei   b: Daicho-kei   c: Boko-kei
d: Kan-kei   e: Shin-kei   f: Sinpo-kei
g: Hi-kei   h: Hai-kei   i: Jin-kei
j: Tan-kei   k: Shocho-kei   l: Sansho-kei The calculated data of the circular graph are displayed on the CRT display 16, or outputted by the printer 17, and stored in the magnetic disc unit 15.

The subject was troubled with nasal hemorrhage and complained of pains at various portions of the body in the first treatment. In the second treatment, the subject still complained of a sustained headache. After the third treatment, the subject complained of no pains and felt relieved in mind and body. The therapist also observed that the subject had a peaceful look and appeared quite relieved of indefinite complaints. Changes in the circular graph pattern of the diagnosis parameters measured with the system of this embodiment also revealed that irregularities in the pattern were remarkable, with a large difference found between the left and right of the body, in the first and second measurements, while these points were much improved in the third measurement, with the pattern having almost no irregularities nor difference between the left and right of the body. This suggests that these diagnosis parameters have a great significance in the diagnosis of a living body.

(Measurement Case 7)

The subject chosen was a 26-year-old male, who had been troubled with very strong dizziness, lowered thinking power and insomnia. The subject was subjected to measurements at the Seiketsu using the system of this embodiment, and the diagnosis parameters AP, BP, $R_1$ and $R_2$ were obtained from the current waveform parameters with the diagnosis parameter arithmetic section 21. The diagnosis arithmetic section 24 reduces these diagnosis parameters into broken-line graphs (a), (b), (c) and (d) shown in FIG. 11, and calculates average values, which are stored in the diagnosis result memory 25. In the broken-line graphs, a–l represent the aforementioned Keiraku, and H indicates that the Seiketsu measured was the Seiketsu of the finger, F indicates that the Seiketsu measured was the Seiketsu of the toe, L indicates that the Seiketsu measured was that of the left hand and foot, and R indicates that the Seiketsu measured was that of the right hand and foot.

The diagnosis parameters measured indicate that the parameter AP on Graph (a) shows extremely low measurements at the Seiketsu on the foot, compared with those at the Seiketsu on the hand, with the ratio of average values for the hand and foot stands at approximately 5:1, compared with the corresponding ratio for a normal person of almost 1:1. This indicates that the subject's sympathetic nerves were strongly excited on the upper half of the body. The parameter BP on Graph (b), on the other hand, shows higher measurements on the foot, compared with those on the hand., This feature with the parameter BP, however, is not so remarkable than with the parameter AP. As for the equivalent circuit parameters $R_1$ and $R_2$ on Graphs (c) and (d), the value for the Boko-kei c (foot) of the parameter $R_2$ was abnormally high, with the remaining values being almost the same values. The parameter $R_1$, on the other hand, had extremely divided values between the hand and foot. That the parameter BP had little difference between the values for the hand and foot is attributable to the fact that both $R_1$ and $R_2$ contribute to BP, as is evident from Equation (5). This measurement case is a good example where the equivalent circuit parameters more clearly demonstrate pathological state of a living body than any other conventional diagnosis parameters.

(Measurement Case 8)

The equivalent circuit parameters $R_1$ and $C_1$ obtained from the measurements at each Seiketsu on the subject chosen for the Measurement Case 7 were plotted on a graph using the diagnosis arithmetic section 24, with the parameter $R_1$ as the abscissa, and the parameter $C_1$ as the ordinate. In the diagnosis standard input section 23, inputted are the average values of the equivalent circuit parameters $R_1$ and $C_1$ obtained by statistically processing the measurement results of many healthy persons.

Figure 12A:
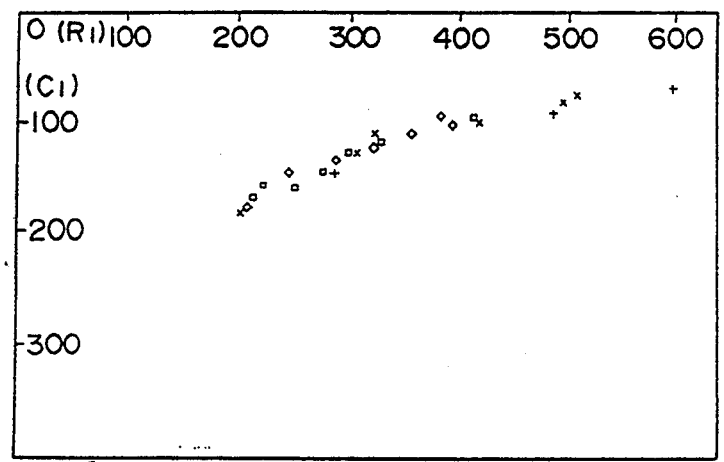
FIGS. 12a, 12b, and 12c are graphs on which the parameters $R_i$ and $C_i$ are plotted.
Figure 12B:
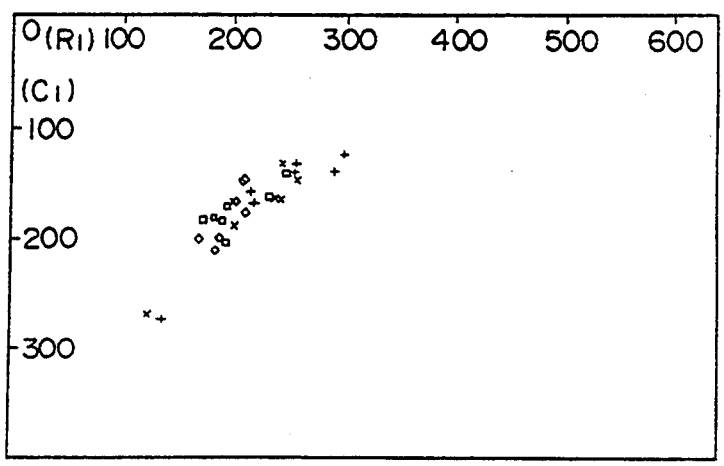
Figure 12C:
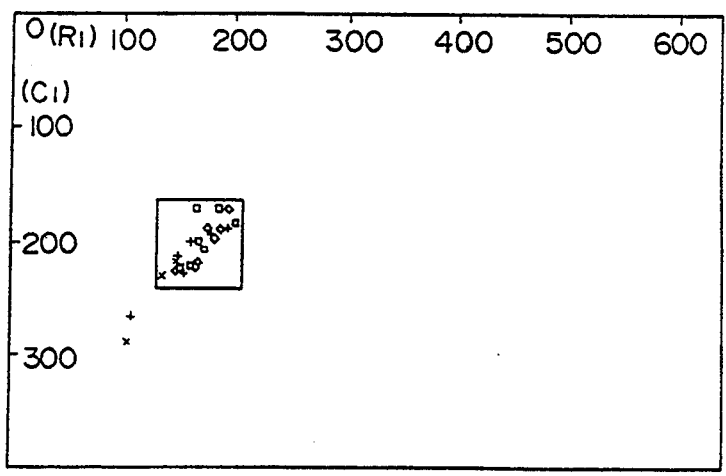

The first measurement case is shown in Graph (c) of FIG. 12. Marks denote measurements at the Seiketsu of the finger, and marks x denote measurements at the Seiketsu of the foot. The results of measurement made on the same subject seven months later are shown in Graph (b) of FIG. 12. Although the subject felt less dizziness and was able to spend an almost comfortable daily life by that time, the $R_1$—$C_1$ plot was such that $R_1$ was larger and $C_1$ smaller than the $R_1$—$C_1$ plot for healthy persons shown in Graph (c) of FIG. 12. In addition, the values measured at the Seiketsu of the finger are separated from the values measured at the Seiketsu of the toe.

On healthy persons, the $R_1$—$C_1$ plot is such that all the points but those for the Hai-kei are concentrated in a region enclosed by a square in Graph (c) of FIG. 12. The values for the Hai-kei, on the other hand, tend to be concentrated in a region where $R_1$ values are slightly lower ($C_1$ values are higher).

(Measurement Case 9)

Areas on the dorsal spine and on both sides of the spine are regions where there are many pressation points not only in the Oriental medical science but also in the Western medical science. In acupuncture/moxibustion medicine, "Tokuei" and the first line of the Boko-kei run over the region. Particularly, on the Boko-kei there lie "Yuketsu" which are diagnosis and treatment points for internal organs.

In chiropractic, too, distortions in sacral, lumbar, thoracic and cervical vertebrae are believed to cause unbalanced tensions throughout the body, contributing to disturbance in various internal organs. More recently, it has been made clear that malocclusion of teeth causes distortions along the cervical and sacral vertebrae.

Consequently, diagnosis along the dorsal spine has an important means in various fields mentioned above.

An example of the diagnosis of the back using the system of this embodiment is shown. The diagnosis points are intervertebral points and points 2.5 cm away from the vertebrae on both sides over a range from the thoracic vertebra $Th_1$ to the sacral vertebra $S_4$ (all these diagnosis points correspond to "Yuketsu" on the back in a acupuncture/moxibustion).

The equivalent circuit parameters $R_1$, $R_2$, $C_1$ and $C_2$ are obtained from current waveform parameters in the diagnosis parameter arithmetic section 21, and graphs $R_1$—$C_1$ and $R_2$—$C_2$ are prepared by plotting resistance values on the abscissa and capacitance values on the ordinate by the diagnosis arithmetic section 24.

Figure 13A:
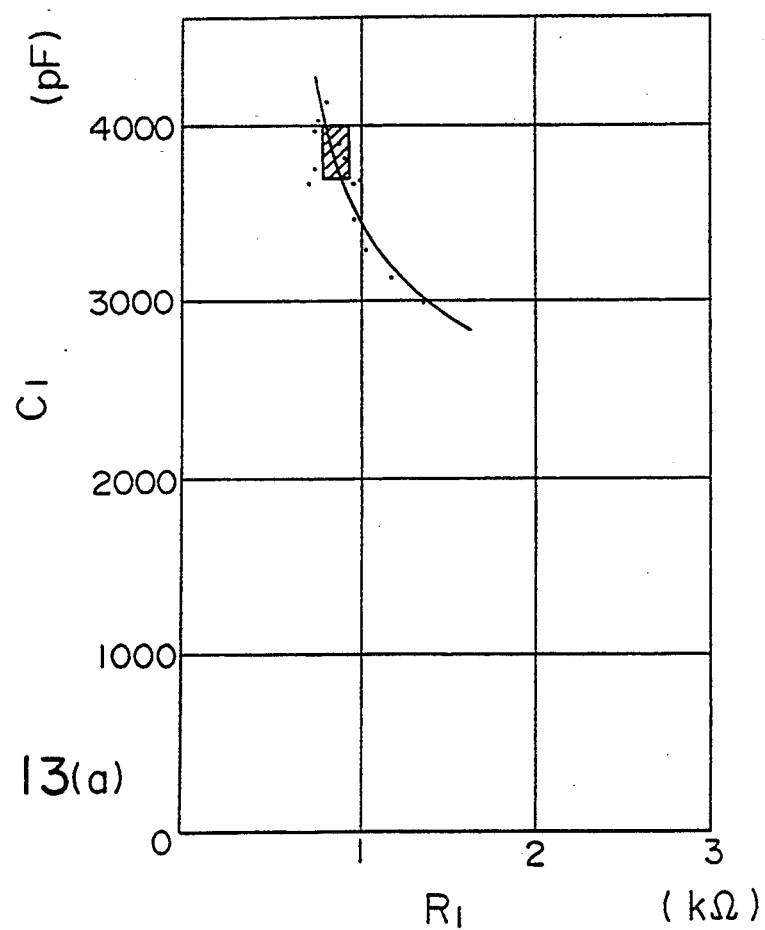
FIGS. 13a and 13b are graphs on which the parameters $R_i$ and $C_i$ are plotted.
Figure 13B:
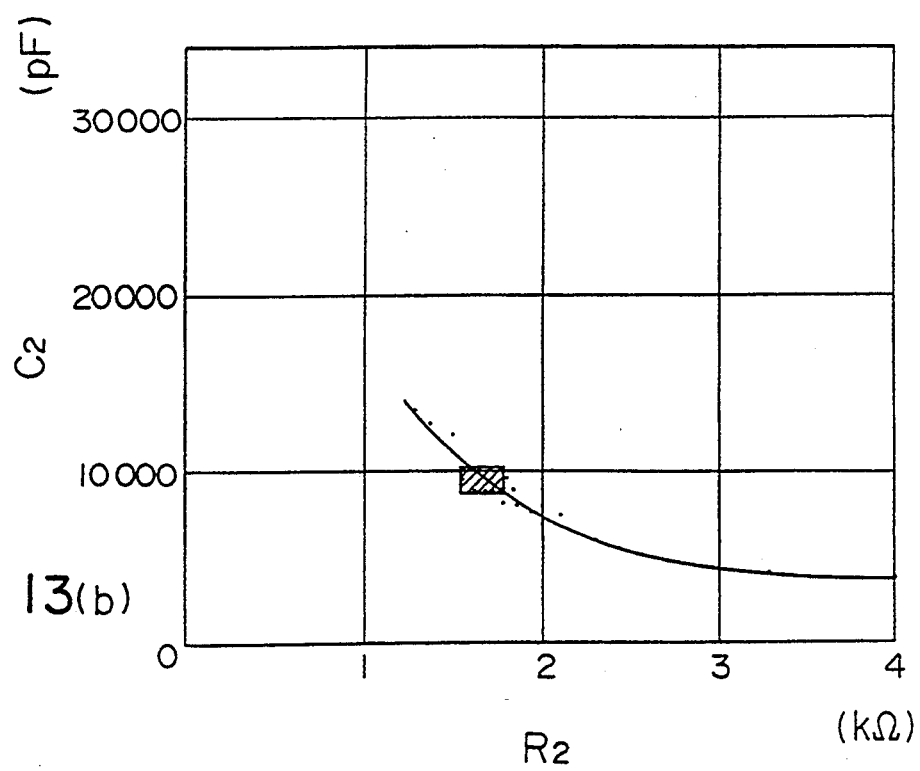

Graph (a) of FIG. 13 is the $R_1$—$C_1$ graph, and Graph (b) of FIG. 13 is the $R_2$—$C_2$ graph, respectively. Most measurements are on a hyperbola, and are concentrated around a given point of the hyperbola. A certain normal region as shown by a hatched portion is set around the aforementioned point through statistical processing in the diagnosis arithmetic section 24, and those points deviating from the region are determined to be abnormal points. Judgement results are stored in the diagnosis result memory 25. The contents of the memory 25 are stirred in the magnetic disc unit 15, and may be displayed on the CRT display 16, or outputted by the printer 17.

Figure 14:
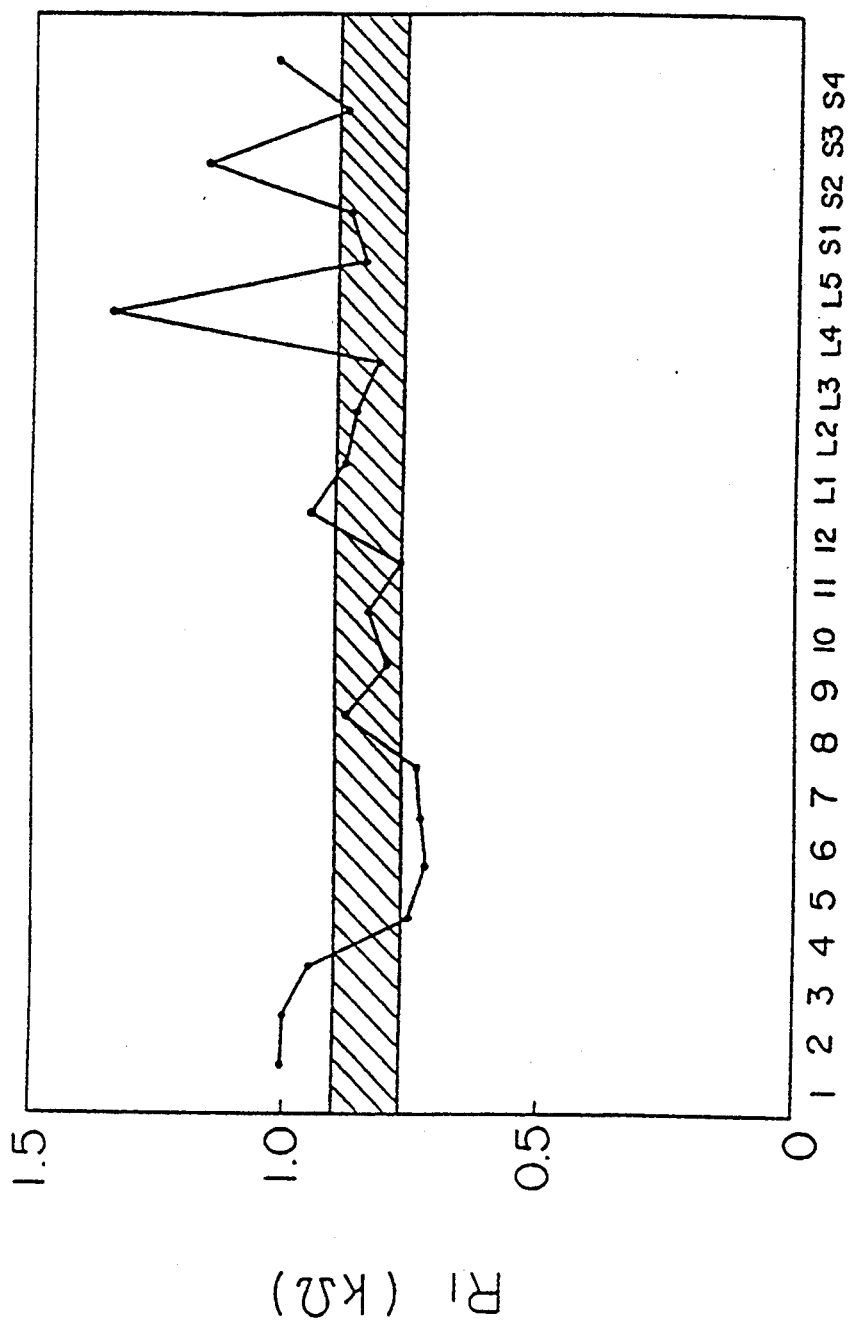
FIG. 14 is a graph illustrating changes in parameters with varied measuring positions.
Figure 15A:
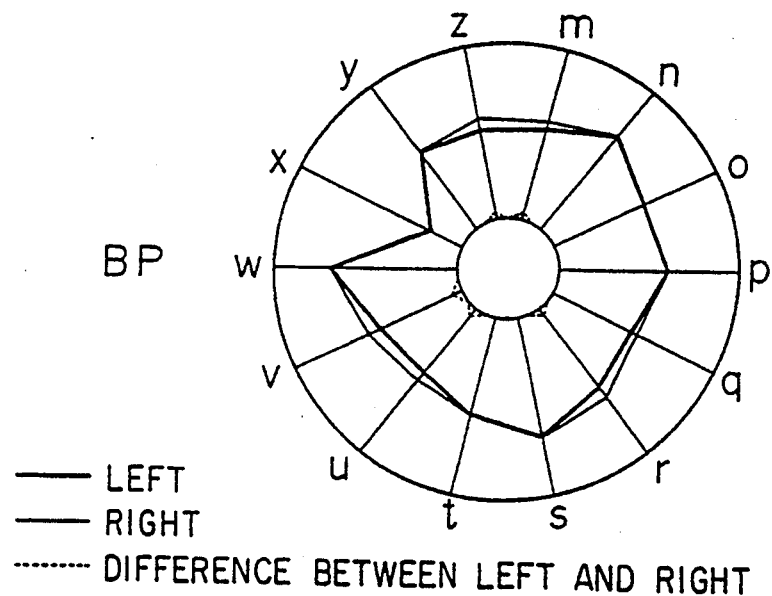
FIGS. 15a and 15b are circular graphs of parameters.
Figure 15B:
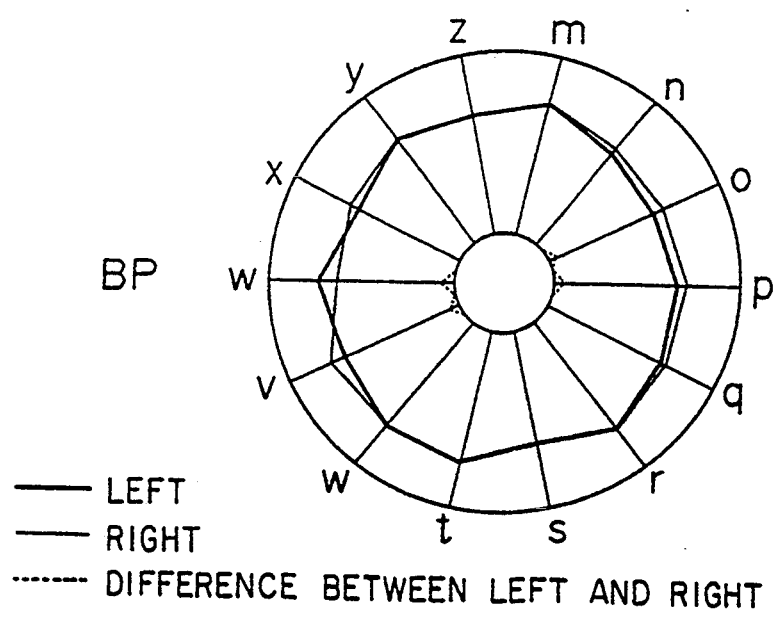
Figure 16:
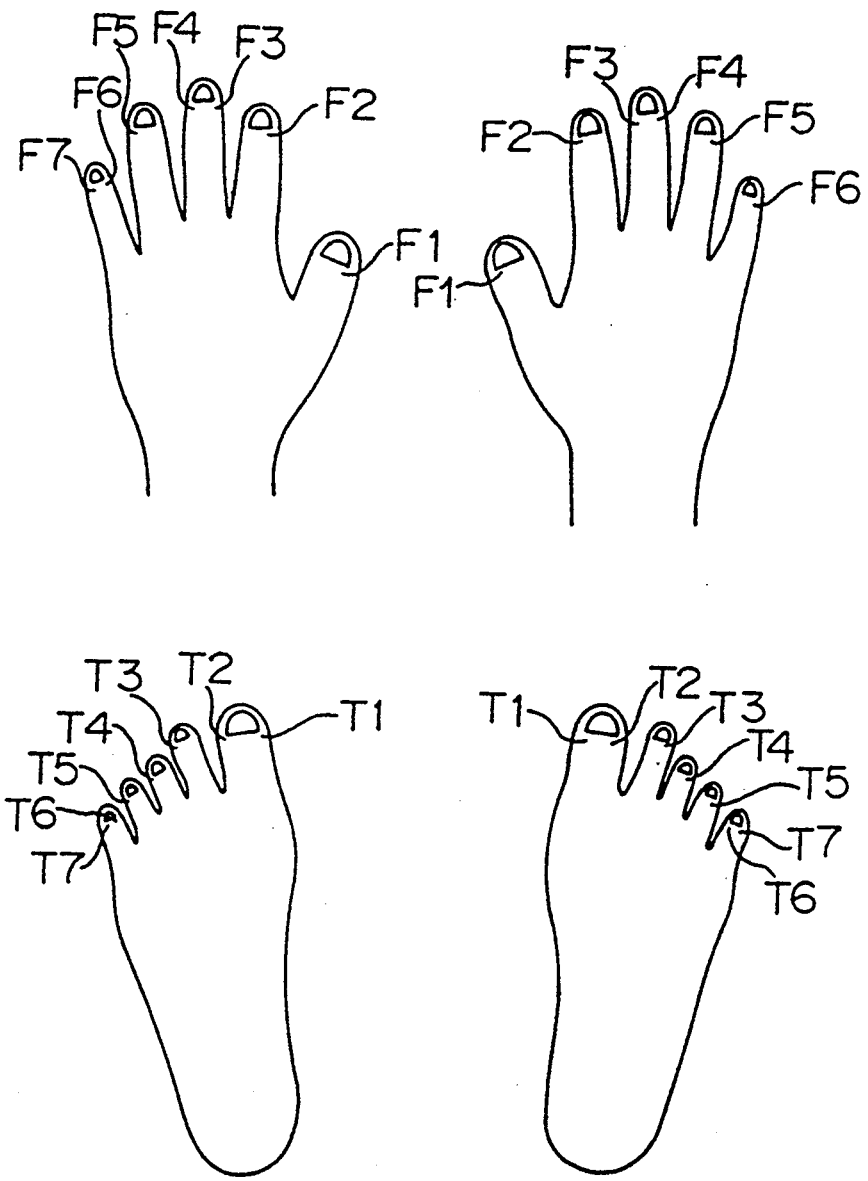
FIGS. 16 is a diagram illustrating the locations of the Seiketsu.

In the diagnosis arithmetic section 24, a graph is prepared by plotting the values of the equivalent circuit parameters $R_1$, $C_1$, $R_2$ and $C_2$ at each measuring points on the ordinate and locations expressed by vertebral numbers on the abscissa. The graph of the parameter $R_1$ is shown in FIG. 14. The numbers ①- ⑫ represent the thoracic vertebrae, ⓛ1 - ⓛ5 the lumbar vertebrae, and Ⓢ1 - Ⓢ4 the sacral vertebrae, respectively. The hatched region corresponds to the normal region in the $R_1$—$C_1$ of Graph (a) of FIG. 13. Those points deviating from this region are determined as abnormal points. Judgement results are stored in the diagnosis result memory 25. The case shown in FIG. 14 reveals that the subject has abnormal points. These points are found in palpation as tenderness, induration, parethesia, and abnormal positions of vertebrae.

tion 24. In the patterns of the circular graph, symbols m-z are the names of the Keiraku, as given below.

m: Gekan   n: Rensen   o: Kyakushujin
p: Taigei   q: Kisha    r: Futotsu
s: Tenso    t: Kankotsu u: Eifu
v: Chokyaku w: Karyo    x: Kyoryo
y: Gakuryo  z: Kyosha The subject chosen was being treated for malocclusion of jaw joints. Graph (a) of FIG. 15 shows the data for a treatment stage where the subject still felt some malocclusion, while Graph (b) of FIG. 15 shows the data for the final stage of treatment in which the subject no longer felt inconvenience in occlusion. The data during treatment apparently have uneven values and poor symmetry between right and left, compared with the data after the completion of treatment. The data after the completion of treatment, on the other hand, have almost the same values for all BP values, and thus the graph pattern assumes almost a true circle.

This measurement case demonstrates that the system of this embodiment is effective in dental diagnosis.

TABLE 6

| Keiraku | Seiketsu | Region | Vertebra | Yuketsu | Entrails |
| --- | --- | --- | --- | --- | --- |
| Hai-kei | Shosho | F1 | 3rd thoracic | Hai-yu | Hai |
| Daicho-kei | Shoyo | F2 | 4th lumbar | Daicho-yu | Daicho |
| Shimpo-kei | Chuko | F3 | 4th thoracic | Ketsuin-yu | Shimpo |
| Kakuyu-kei |  | F4 | 7th thoracic | Kaku-yu |  |
| Sansho-kei | Kanko | F5 | 1st lumbar | Sansho-yu | Sansho |
| Shin-kei | Shoko | F6 | 5th thoracic | Shin-yu | Shin |
| Shocho-kei | Shotaku | F7 | 1st sacral | Shocho-yu | Shocho |
| Hi-kei | Inpaku | T1 | 11th thoracic | Hi-yu | Hi |
| Kan-kei | Taiton | T2 | 9th thoracic | Kan-yu | Kan |
| I-kei | Reida | T3 | 12th thoracic | I-yu | I |
| Hachiyu-kei |  | T4 | 8th thoracic |  |  |
| Tan-kei | Kyoin | T5 | 10th thoracic | Tan-yu | Tan |
| Jin-kei |  | T6 | 2nd lumbar | Jin-yu | Jin |
| Boko-kei | Shiin | T7 | 2nd sacral | Boko-yu | Boko |

(Measurement Case 10)

Recent studies are gradually making clear that malocclusion of teeth causes distortion of cervical vertebrae, which develops in the thoracic, lumbar and sacral vertebrae, adversely affecting the entire body. Such distortion also causes over-tension of muscles and abnormal excitation of autonomic nerves at various location of the body, and even abnormality in the functions of various internal organs.

Malocclusion most frequently causes a strong tension in muscles of mastication, sterno-cleidomastoid, muscles around the jaws, the face, and the neck. It also causes a strong tension around the thoracic vertebrae above the cervical vertebrae. These tension naturally affect the surface of the skin around the area where tensions are caused. Consequently, measurement of electrical characteristics of the layers near the skin by means of the system of this embodiment is effective in the diagnosis of teeth occlusion.

To confirm this, measurement of current waveforms was conducted using the system of this embodiment by selecting the Keiketsu existing at the start and stop of muscles of mastication and other muscles having close relations with mastication as measuring points. The parameter BP was obtained by the diagnosis parameter arithmetic section 21, and a circular graph, as shown in FIG. 15, was prepared by the diagnosis arithmetic sec- Clinical data accumulated after long years of study by the present inventor et al reveal that a Seiketsu having a small parameter BP indicates an abnormal slip of the vertebra to which the Seiketsu corresponds. That is, if the left of a Keiraku is energy-deficient, or (that is, the parameter BP assumes a smaller value in relation to the entire Keiraku), the spine is distorted towards the left, centering around the vertebra corresponding to that Keiraku, and the pelvice is also distorted accordingly. If the right of a Keiraku is energy-deficient, the spine is distorted towards the right, centering around the vertebra corresponding to that Keiraku, and the pelvice is also distorted accordingly. If the right and left of a Keiraku are energy-deficient, there is an abnormality in the antero-posterior direction of the vertebra corresponding to that Keiraku, and accordingly an abnormality appears on the cer-vical vertebra.

An example of estimation of the distortion of the spine using the system of this embodiment is shown here.

The parameter $BP_{ij}$ is calculated by the diagnosis parameter arithmetic section 21 by measuring the Seiketsu and determining the current waveform parameters by the waveform analyzing section 11. The subscript i denotes the number of a Keiraku, and the subscript j denotes distinction between left (L) and right (R).

The ratio of the parameter $BP_{ij}$ thus obtained and the standard parameter $BP_i^s$ obtained from the average of the measurement results for a statistically sufficient number of normal person, $$BP_{ij}^* = \frac{BP_{ij}}{BP_i^s}$$

is calculated by the diagnosis arithmetic section 24. The standard $BP_i^s$ is stored in the diagnosis standard input section 23.

In the diagnosis arithmetic section 24, the average of the left and right is calculated.

$$\overline{BP_i^*} = \frac{BP_{iL}^* + BP_{iR}^*}{2}$$

Then, the $BP_{iL}^*$, $BP_{iR}^*$ and $BP_i^*$ values for 14 Keiraku are arranged in the descending order of size, and the least five values are taken.

Table 7 shows the Keiraku having the least five BP values for each of the cases where the left Keiraku is energy-deficient, or the right Keiraku is energy-deficient, or both the right and left Keiraku are energy-deficient.

TABLE 7

| Order | Left "Kyo" | Right "Kyo" | Left/right "Kyo" |
|---|---|---|---|
| 1 | Hai-kei | Shin-kei | Hai-kei |
| 2 | Daicho-kei | Shocho-kei | Daicho-kei |
| 3 | Hachiyu-kei | Hai-Kei | Shin-kei |
| 4 | Tan-lei | Daicho-kei | Shocho-kei |
| 5 | I-kei | Kakuyu-kei | Tan-kei |

When estimating the horizontal slip of the spine and the inclination of the ilium based on the example shown in Table 7, first the third thoracic vertebra is chosen since the left "Kyo" (which has the least BP* value) is the "Hai-kei" (Lung Keiraku), which corresponds to the third thoracic vertebra according to Table 6. That is, the third thoracic vertebra is shifted leftwards by 6 units, the second and fourth thoracic vertebrae immediately above and below the third thoracic vertebra are shifted leftwards by 5 units, the first and fifth vertebrae by 4 units, the seventh cervical vertebra and the sixth thoracic vertebra by 3 units, the sixth cervical vertebra and the seventh thoracic vertebra by 2 units, and the fifth cervical vertebra and the eighth vertebra by 1 unit, respectively. The results of these shifts are shown in FIG. 17.

Since the "Daicho-kei" (Colon Keiraku) is the second "Kyo" in Table 7, the fourth lumbar vertebra, which corresponds to the "Daicho-kei" in Table 6, is shifted leftwards by 5 units, and other vertebrae above and below the fourth lumbar vertebra are shifted by the number of units which decreases at decrements of one unit per vertebra in the same manner as described above.

Thus, shifts are caused in the same procedures up to the least fifth left "Kyo" in accordance with Table 8.

TABLE 8

| Left (right) "Kyo" | Units of shift |
|---|---|
| 1st rank | 6 units |
| 2nd rank | 5 units |
| 3rd rank | 4 units |
| 4th rank | 3 units |
| 5th rank | 2 units |

Next, similar processing is performed for the right "Kyo."

The entire image of shifts towards the right and left of the spine is determined by adding up all the shifts of vertebrae made in the foregoing processing.

The inclination of the ilium is given in proportion to the shifting of the first and fifth sacral vertebrae. The direction of inclination is the left-side up if the fifth sacral vertebra is shifted leftwards with respect to the first sacral vertebra, and the right-side up in the reverse case.

Figure 18:
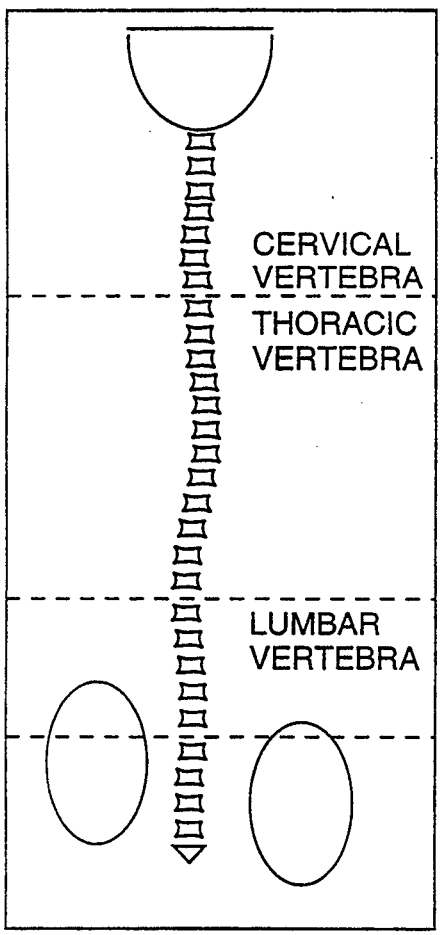
FIG. 18 is a graphic representation of the distortion of the spine and the ilium.

The distortions of the spine and the ilium eventually obtained in the diagnosis arithmetic section 24 are stored in the diagnosis result memory 25, and displayed on the CRT display 16. A typical graphic representation is shown in FIG. 18, in which the spine is viewed from the back side of the body.

Next, estimation of abnormality in the antero-posterior direction of the vertebra by the diagnosis arithmetic section 24 will be described, referring to the example given in Table 7.

In the "Ryo-kyo" (energy-deficient on both sides) column in Table 7, given are the left-right average $BP_i^*$ values in the descending order of size. In accordance with Table 6 indicating the correspondence of Keiraku and vertebrae, abnormalities of positions in the antero-posterior direction are estimated as follows.

"Hai-kei" (Lung Keiraku)—3rd thoracic vertebra

"Daicho-kei" (Colon Keiraku)—4th lumbar vertebra

"Shin-kei" (Cardiac Keiraku)—5th thoracic vertebra

"Shocho-kei" (Small intestine Keiraku)—1st sacral vertebra

"Tan-kei" (Gallbladder Keiraku)—10th thoracic vertebra

When the "Shocho-kei" (corresponding to the 1st sacral vertebra) and "Boko-kei" (corresponding to the 2nd sacral vertebra) are in the "Ryo-kyo," abnormalities are expected in the 1st, 2nd and 5th cervical vertebrae.

Figure 19:
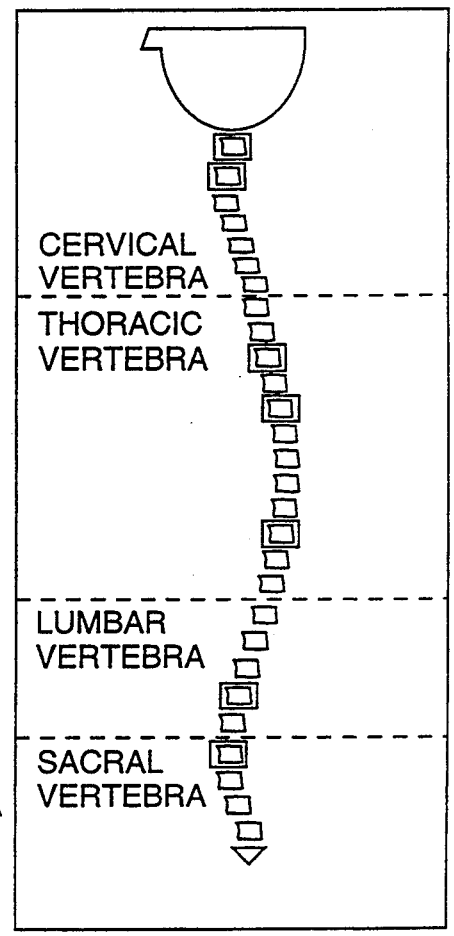
FIG. 19 is a graphic representation of the antero-posterior abnormality of the vertebra.

The above judgement results are stored in the diagnosis result memory 25, and displayed in the form of graphic representation on the CRT display 16. A typical graphic representation is shown in FIG. 19. This graphic representation is the spine viewed from the side of the body. In the figure, the vertebrae enclosed by squares are estimated to abnormal in position with respect to the immediately above and below that vertebra.

EMBODIMENT 3

Figure 20:
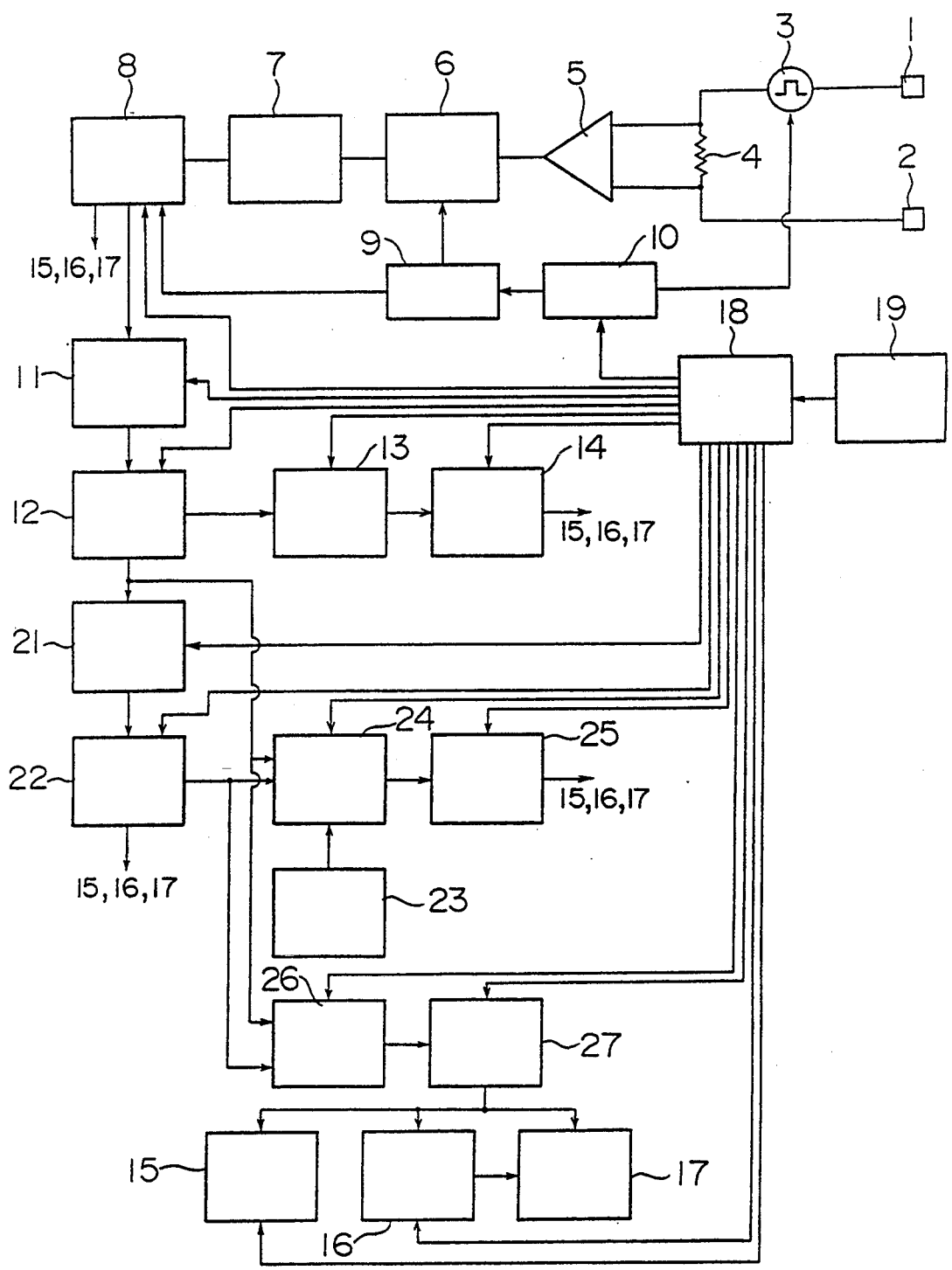
FIG. 20 is a diagram illustrating the third embodiment of this invention.

FIG. 20 is a block diagram of the third embodiment of the biological information measuring system according to this invention. This embodiment is essentially the same as the biological information measuring system shown in FIG. 7, except that a mapping arithmetic section 26 and a mapping result memory 27 are added to the system shown in FIG. 7.

The mapping arithmetic section 26 analyzes the measurement results at a finite number of arbitrary measuring points distributed over a certain area of the surface of a living body selected as a subject, reads from the waveform parameter memory 12 the current waveform parameters obtained by the above analysis, or reads from the diagnosis parameter memory 22 the parameters obtained by calculating the current waveform parameters; divides the distance between the measuring points further into finer meshes in accordance with the spatial arrangement of the measuring points, and calculates the parameter values at the intersecting points of the meshes using a certain interpolation function; divides the interval between the minimum and maximum values into certain classes; and performs arithmetic to impart a certain color or a certain density or a certain pattern to each class. Furthermore, the mapping arithmetic section 26 performs arithmetic to obtain contour lines by enclosing regions to which values for a certain class are concentrated with lines.

The mapping result memory 27 stores the arithmetic results of the mapping arithmetic section 26. The stored data are stored in the magnetic disc unit 15, and can be displayed on the CRT display 16, or outputted by the printer 17.

The operation of this embodiment will be described on the basis of the following measuring cases.

(Measuring Case 12)

In this measuring case, a topograph is prepared from the current waveform parameters as the measurement results. First, the measuring area is divided into 5×5, 7×7, 7×9 and 9×9 meshes, and the intersecting points of these meshes are used as measuring points. The meshes here need not be rectangles. Current waveform parameters are obtained through the analysis of measurement results at each measuring point in the waveform analyzing section 11, and stored in the waveform parameter memory 12. Then, equivalent circuit parameters or transient characteristic parameters are obtained by the diagnosis parameter arithmetic section 21 as necessary, in the same manner as shown with reference to the measurement cases described earlier.

Now, an arbitrary type is designated from among these parameters, and sent to the mapping arithmetic section 26 as a means for obtaining a topograph. In the mapping arithmetic section 26, an interpolation function is first selected, and interpolation calculation is performed by dividing the minimum unit area of meshes further into finer meshes (into 100 meshes in the lateral and longitudinal directions). As an interpolation function, a straight line, a quadratic curve, or a Gaus function may be used. The calculation results are stored in the mapping result memory 27.

Upon completion of all the interpolation calculations, a topograph of these parameters can be displayed on the CRT display 16 in an appropriate mode, such as a three-dimensional display using pattern coding, color coding, contour lines or meshes, or outputted by the printer 17 as necessary.

Figure 21:
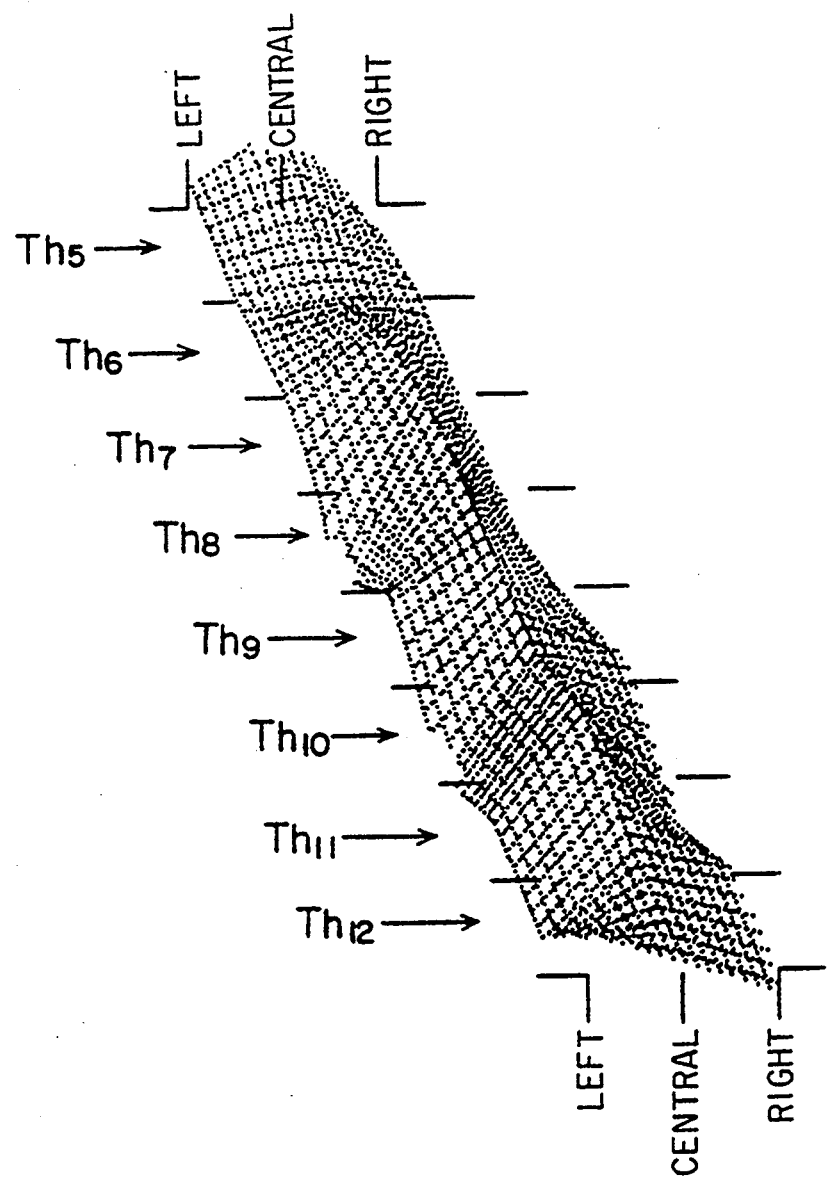
FIG. 21 is a diagram illustrating an example of the topograph.

As a specific example, the application of this embodiment to the spine is shown. The subject has a visible slip between the fifth thoracic vertebra Th$_5$ and the sixth thoracic vertebra Th$_6$. A topograph of the current waveform parameter I$_1^0$ from the lower part of the fourth thoracic vertebra Th$_4$ to the lower part of the 12th thoracic vertebra Th$_{12}$ when measuring points are set between the spinous extuberances on the spine and on both sides of the spine (on lines 2.5 cm away from the spinal line in both directions) is shown in FIG. 21. The topograph in the figure indicates that there is a depression between the 5th thoracic vertebra Th$_5$ and the 6th thoracic vertebra Th$_6$.

(Measurement Case 13)

This measurement case is a case where nasal diseases can be clearly identified by topographic representation. The subject had a nasal polyp in his left nasal cavity and was troubled with nasal congestion.

Figure 22A:
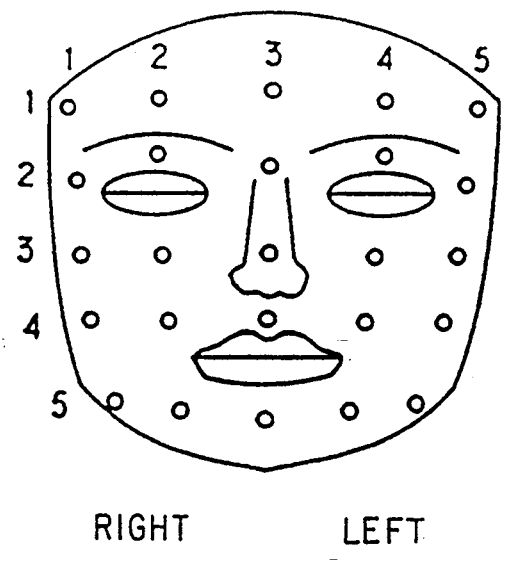
FIG. 22A is a diagram illustrating measuring positions.
Figure 22B:
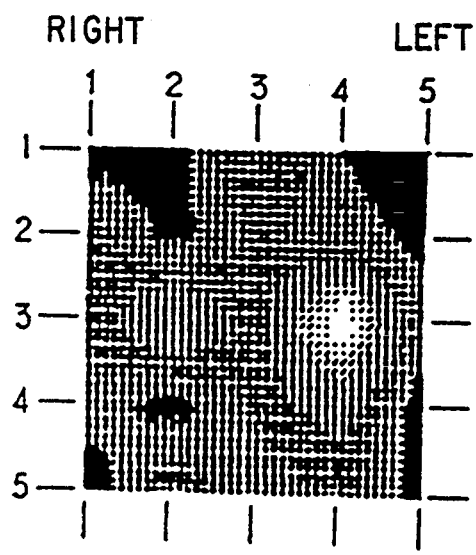
FIG. 22B is a diagram illustrating the topograph.

In the mapping arithmetic section 26, current waveform parameters were taken out of the waveform parameter memory 12, and the equivalent circuit parameters or the transient characteristic parameters, both of which were obtained through calculation, were taken out of the diagnosis parameter memory 22, and a topograph was prepared for each set of the parameters. FIG. 22A is a diagram illustrating measuring points (shown by o marks) on the face of the subject, and FIG. 22B is a topograph for the parameter AP, for example. Observation of topographs for these parameters revealed that an abnormal asymmetry was found on the area of the nose in the topographs for the parameters I$_1^0$, I$_2^0$, AP and BP. In addition, relatively lower values were observed in the left part of the face in the topographs for the parameters I$_1^0$ and I$_2^0$, while higher values were found in the left part of the face in the topograph for the parameter I$_{DC}$.

(Measurement Case 14)

An example of the application of topographic representation to dorsal diagnosis is shown here. Diagnosis of the back surface of the body is an important diagnosis method in both Oriental and Western medical sciences.

Figure 23:
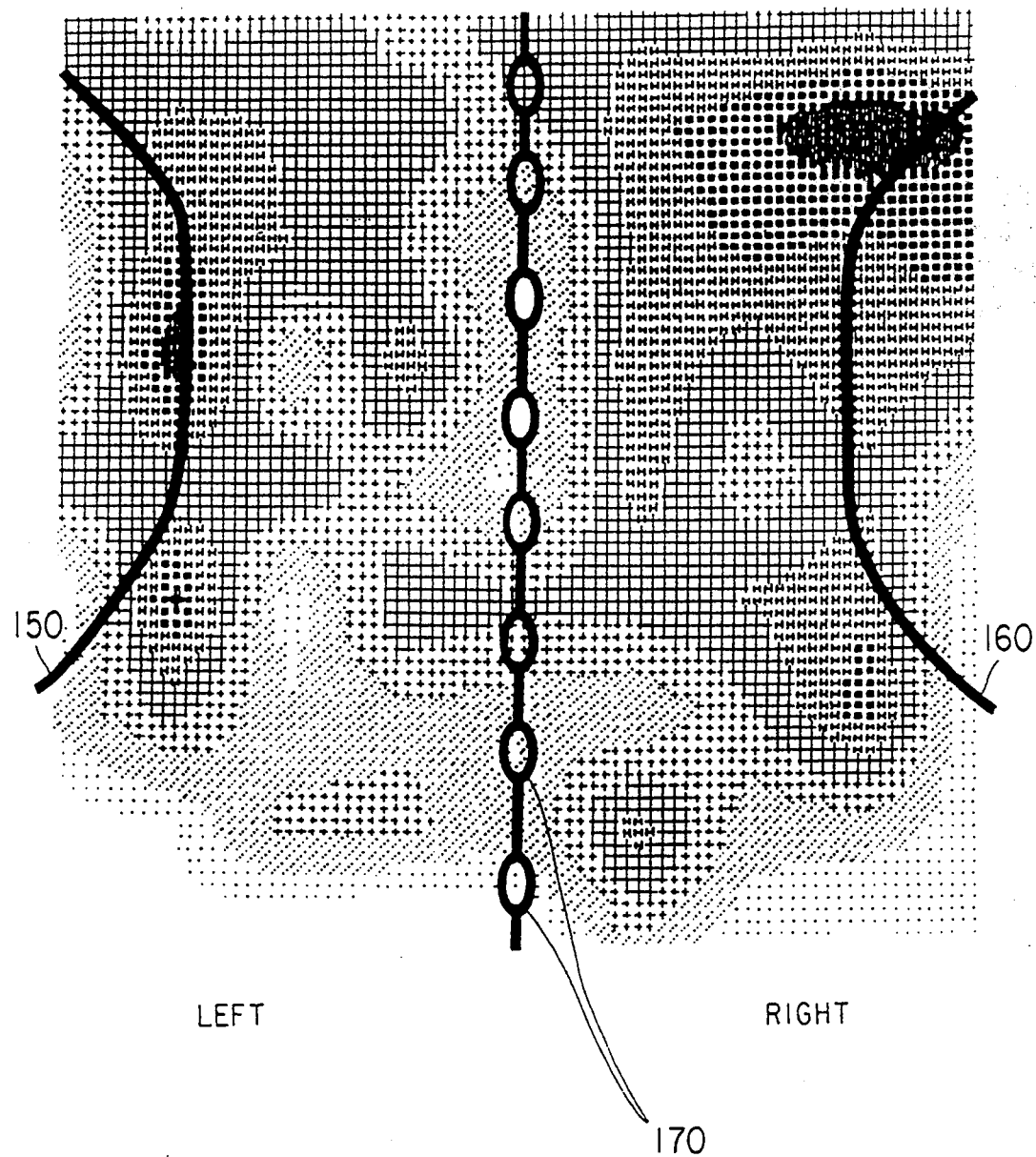
FIG. 23 is a diagram illustrating another example of the topograph.

The subject in this case complained considerably strong stiffness in the shoulders. The topograph for the parameter I$_1^0$ shown in FIG. 23 indicates that the I$_1^0$ values are low along the inner edges of the scapulae 150 and 160, and at the upper corner of the right scapula. Palpation of those regions revealed that strong pains were observed in these parts and indurations in the subcutaneous tissues. In FIG. 23, 170 denotes a spinous extuberance on the spine.

Although various embodiments of this invention have been described in the foregoing, this invention is not limited to these embodiment and various changes and modifications may be made in the invention without departing from the spirit and scope thereof. In the second embodiment shown in FIG. 7, for example, the waveform synthesizing section 13 and the synthesized waveform memory 14 may be omitted. In the third embodiment shown in FIG. 20, the waveform synthesizing section 13, the synthesized waveform memory 14, the diagnosis standard input section 23, the diagnosis arithmetic section 24 and the diagnosis result memory 25 may be omitted.

INDUSTRIAL APPLICABILITY

Since the biological information measuring system of this invention analyzes current waveforms, particularly in terms of equivalent circuits in accordance with the structure of the skin, the application of the system of this invention to diagnosis is not necessarily limited to acupuncture/moxibustion medicine, but it is available for widespread use in modern medical science.

Moreover, finding correct equivalent circuits for the skin not only has an important bearing in terms of electrophysiology but also opens up a very wide range of practical applications. In other words, the system of this invention can be used for the electrophysiological analysis of the surface of living bodies, whether animals or plants. Thus, the biological information measuring system of this invention is available for use in inspecting the freshness of fruits, monitoring the growth of agricultural crops and many other applications.

We claim:

1. An apparatus for measuring electrical characteristics of a body, the apparatus comprising:

a first electrode adapted to be positioned on the body;

a second electrode adapted to be positioned on the body and spaced from said first electrode;

voltage pulse means for applying a substantially rectangular voltage pulse across said first and second electrodes;

waveform recording means for recording a current I(t) flowing through said first and second electrodes during said voltage pulse as a current waveform;

waveform analyzing means for analyzing said current waveform to determine parameters $I_i^0$, $\tau_i$, and $I_{DC}$, which relates to said current waveform by the formula $$I(t) = \sum_{i=1}^{n} I_i^0 e^{-(t/\tau_1)} + I_{DC}$$

where, n = a positive integer greater than one, $I_i^0$ = a plurality of waveform parameters, t = time, $\tau$ = a plurality of time constants, $I_{DC}$ = a DC component of said waveform, said parameters $I_i^0$, $\tau_i$, and $I_{DC}$ representing the electrical characteristics of the body.

2. An apparatus in accordance with claim 1, further comprising:

means for storing said parameters $I_i^0$, $\tau_i$, and $I_{DC}$;

means for reproducing an approximation of said current waveform from said stored parameters $I_i^0$, $\tau_i$, and $I_{DC}$.

3. An apparatus in accordance with claim 1, wherein:

said waveform analyzing means determines resistance and capacitance values of a portion of said body between said first and second electrodes by representing the portion of the body by an equivalent circuit including a plurality i of parallel legs, one of said plurality of parallel legs including a resistor $R_{DC}$ and each of a remainder of said plurality of parallel legs having a resistor $R_i$ and capacitor $C_i$ in series, a magnitude of each of said resistors $R_i$ and capacitors $C_i$ being determined by ti $R_i = V/(I_i^0 e^{-(t/\tau_i)})$ $C_i = (I_i^0 \cdot e^{-(t/\tau_i)} \tau_i)/V$ $R_{DC} = V/I_{DC}$ where V is a voltage of said voltage pulse.

4. An apparatus in accordance with claim 3, wherein:

said waveform analyzing means determines a pre-polarization current BP of the body by the formula $$BP = \sum_{i=1}^{n} I_i^0 + I_{DC}$$

said waveform analyzing means determines a post-polarization current AP of the body by the formula $AP = I_{DC}$ said waveform analyzing means determines a total charge IQ of said current waveform by the formula $$IQ = \sum_{i=1}^{n} \tau_i I_i^0$$

said waveform analyzing means determines an attenuation time TC of said current waveform by the formula $$TC = \frac{\sum_{i=1}^{n} I_i^0}{\sum_{i=1}^{n} \frac{I_i^0}{\tau_i}}.$$

5. An apparatus in accordance with claim 4, further comprising:

means for comparing one of said parameters $I_i^0$, $\tau_i$, $I_{DC}$, $R_i$, $C_i$, $R_{DC}$, BP, AP, IQ and TC with a predetermined value for detecting abnormalities.

6. An apparatus in accordance with claim 5, wherein:

said first and second electrodes are movable to a plurality of different location on the body; and said waveform analyzing means determines the electrical characteristics at each of said plurality of different locations and averages one of the electrical characteristics over said plurality of different locations to create said predetermined value.

7. An apparatus in accordance with claim 5, wherein:

said first and second electrodes are adapted to be positioned on a normal living body; and said waveform analyzing means statistically processes one of the electrical characteristics over said plurality of different locations to create said predetermined value.

8. An apparatus in accordance with claim 4, wherein:

said first and second electrodes are movable to a plurality of measuring positions on the body;

said waveform analyzing means determines the electrical characteristics at each of said plurality of measuring positions and uses an interpolation function to determined the electrical characteristics between said plurality of measuring positions and also graphically displays the electrical characteristics topographically.

9. A method for measuring electrical characteristics of a body, the method comprising the steps of:

placing a first electrode on the body;

placing a second electrode on the body and spaced from said first electrode;

applying a voltage pulse across said first and second electrodes;

recording a current flowing through said first and second electrodes during said voltage pulse as a current waveform;

analyzing said current waveform to represent said current waveform by the formula $$I(t) = \sum_{i=1}^{n} I_i^0 e^{-(t/\tau_1)} + I_{DC}$$

where, n = a positive integer greater than one, $I_i^0$ = a plurality of waveform parameters, t = time, $\tau$ = a plurality of time constants, $I_{DC}$ = a DC component of said waveform, in order to determine parameters $I_i^0$, $\tau_i$, and $I_{DC}$ which represent the electrical characteristics of the body.

10. A method in accordance with claim 9, further comprising:

storing said parameters $I_i^0$, $\tau_i$, and $I_{DC}$;

reproducing an approximation of said current waveform from said stored parameters $I_i^0$, $\tau_i$, and $I_{DC}$.

11. A method in accordance with claim 9, further comprising:

determining resistance and capacitance values of a portion of said body between said first and second electrodes by representing the portion of the body by an equivalent circuit including a plurality i of parallel legs, one of said plurality of parallel legs including a resistor $R_{DC}$ and each of a remainder of said plurality of parallel legs having a resistor $R_i$ and capacitor $C_i$ in series, a magnitude of each of said resistors $R_i$ and capacitors $C_i$ being determined by $$R_i = V/(I_i^0 e^{-(t/\tau_i)})$$

$$C_i = (I_i^0 \cdot e^{-(t/\tau_i)} \tau_i)/V$$

$$R_{DC} = V/I_{DC}$$

where V is a voltage of said voltage pulse.

12. A method in accordance with claim 11, further comprising:

comparing magnitudes of one of said $R_i$, $C_i$ and $R_{DC}$ with a predetermined value for detecting abnormalities.

13. A method in accordance with claim 9, further comprising:

determining a pre-polarization current BP of the body by the formula $$BP = \sum_{i=1}^{n} I_i^0 + I_{DC}$$

determining a post-polarization current AP of the body by the formula $$AP = I_{DC}$$

determining a total charge IQ of said current waveform by the formula $$IQ = \sum_{i=1}^{n} \tau_i I_i^0$$

determining an attenuation time TC of said current waveform by the formula $$TC = \frac{\sum_{i=1}^{n} I_i^0}{\sum_{i=1}^{n} \frac{I_i^0}{\tau_i}}$$

14. A method in accordance with claim 13, further comprising:

comparing magnitudes of one of said BP, AP, IQ and TC with a predetermined value for detecting abnormalities.

15. A method in accordance with claim 9, further comprising:

comparing one of said parameters $I_i^0$, $\tau_i$, and $I_{DC}$ with a predetermined value for detecting abnormalities.

16. A method in accordance with claim 15, further comprising:

moving said first and second electrodes to a plurality of different location on the body and determining the electrical characteristics at each of said plurality of different locations;

averaging one of the electrical characteristics over said plurality of different locations to create said predetermined value.

17. A method in accordance with claim 15, further comprising:

placing said first and second electrodes on a normal living body;

statistically processing one of the electrical characteristics over said plurality of different locations to create said predetermined value.

18. A method in accordance with claim 9, further comprising:

providing a plurality of measuring positions on the body;

moving said first and second electrodes to said plurality of measuring positions and determining the electrical characteristics at each of said plurality of measuring positions;

using an interpolation function to determined the electrical characteristics between said plurality of measuring positions;

graphically displaying the electrical characteristics topographically.

* * * * *